US011091434B2

(12) United States Patent
Lerer et al.

(10) Patent No.: US 11,091,434 B2
(45) Date of Patent: *Aug. 17, 2021

(54) TYPE III DEIODINASE INHIBITORS AND USES THEREOF

(71) Applicants:HADASIT MEDICAL RESEARCH SERVICES AND DEVELOPMENT LTD., Jerusalem (IL); INDIAN INSTITUTE OF SCIENCE, Bangalore (IN)

(72) Inventors: Bernard Lerer, Alon Shvut (IL); Mugesh Govindasamy, Bangalore (IN); Tzuri Lifschytz, Jerusalem (IL)

(73) Assignees: HADASIT MEDICAL RESEARCH SERVICES AND DEVELOPMENT LTD., Jerusalem (IL); INDIAN INSTITUTE OF SCIENCE, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/553,647

(22) Filed: Aug. 28, 2019

(65) Prior Publication Data

US 2019/0389799 A1    Dec. 26, 2019

Related U.S. Application Data

(63) Continuation of application No. 15/126,023, filed as application No. PCT/IL2015/050277 on Mar. 16, 2015, now Pat. No. 10,435,365.

(60) Provisional application No. 61/953,846, filed on Mar. 16, 2014, provisional application No. 62/097,142, filed on Dec. 29, 2014.

(51) Int. Cl.
| | |
|---|---|
| *A61K 31/40* | (2006.01) |
| *C07D 207/456* | (2006.01) |
| *C07D 405/06* | (2006.01) |
| *C07D 517/04* | (2006.01) |
| *A61P 25/24* | (2006.01) |
| *A61P 35/00* | (2006.01) |
| *A61K 31/4015* | (2006.01) |
| *A61K 31/4025* | (2006.01) |
| *A61K 31/402* | (2006.01) |

(52) U.S. Cl.
CPC .......... *C07D 207/456* (2013.01); *A61P 25/24* (2018.01); *A61P 35/00* (2018.01); *C07D 405/06* (2013.01); *C07D 517/04* (2013.01); *A61K 31/402* (2013.01); *A61K 31/4015* (2013.01); *A61K 31/4025* (2013.01)

(58) Field of Classification Search
CPC .......................... A61K 31/4015; A61K 31/402
USPC ...................................................... 514/425
See application file for complete search history.

(56) References Cited

U.S. PATENT DOCUMENTS

| | | | |
|---|---|---|---|
| 2,865,730 | A | 12/1958 | Gates |
| 3,129,225 | A | 4/1964 | Shapiro |
| 4,582,849 | A | 4/1986 | Marzolph |
| 5,039,696 | A | 8/1991 | Niwata |
| 8,304,401 | B2 | 11/2012 | St. Germain et al. |
| 10,435,365 | B2* | 10/2019 | Lerer .................. A61P 25/24 |
| 2004/0152721 | A1 | 8/2004 | Prudhomme |
| 2005/0171076 | A1 | 8/2005 | Meggers |
| 2008/0039518 | A1 | 2/2008 | Michejda |
| 2009/0275547 | A1 | 11/2009 | Meggers |

FOREIGN PATENT DOCUMENTS

| | | |
|---|---|---|
| CN | 103113280 A | 5/2013 |
| CN | 103130790 A | 6/2013 |
| DE | 3513715 A1 | 10/1986 |
| FR | 3008408 A1 | 1/2015 |
| GB | 818192 A | 8/1959 |
| GB | 02451858 A | 2/2009 |
| WO | 8704321 A2 | 7/1987 |
| WO | 9318766 A1 | 9/1993 |
| WO | 9851303 A1 | 11/1998 |
| WO | 03099105 A2 | 12/2003 |
| WO | 2004083202 A1 | 9/2004 |
| WO | 2005070024 A2 | 8/2005 |
| WO | 2005081972 A2 | 9/2005 |
| WO | 2006028835 A2 | 3/2006 |
| WO | 2008140713 A1 | 11/2008 |
| WO | 2009015366 A2 | 1/2009 |
| WO | 2010027965 A1 | 3/2010 |
| WO | 2010110974 A1 | 9/2010 |
| WO | 2013121175 A1 | 8/2013 |
| WO | 2013132268 A1 | 9/2013 |
| WO | 2014085545 A1 | 6/2014 |

OTHER PUBLICATIONS

Goemann et al. "Current concepts and challenges to unravel the role of iodothyronine deiodinase in human neoplasia," Endocrine-related Cancer, 2019, vol. 25 pp. R625-R645 (Year: 2019).*
Lifschytz et al., (2006) Basic mechanisms of augmentation of antidepressant effects with thyroid hormone. Current Drug Targets 7(2): 203-210.
Lifschytz et al., (2011) Effect of triiodothyronine on antidepressant screening tests in mice and on presynaptic 5-HT1A receptors: mediation by thyroid hormone α receptors. Journal of Pharmacology and Experimental Therapeutics 337(2): 494-502.
Link et al., (1996) Staurosporine and ent-Staurosporine: The First Total Syntheses, Prospects for a Regioselective Approach, and Activity Protiles1. Journal of the American Chemical Society 118(12): 2825-2842.

(Continued)

*Primary Examiner* — Shengjun Wang
(74) *Attorney, Agent, or Firm* — Rothwell, Figg, Ernst & Manbeck, P.C.

(57) ABSTRACT

The present invention relates to compounds that inhibit the activity of Type III deiodinase (DIO3). The present invention further relates to methods for treating or preventing depression, depression associated with other psychiatric or general medical diseases or conditions, condition amenable to treatment with known anti-depressants and cancer, particularly by using the compounds of the invention.

16 Claims, 13 Drawing Sheets

(56) References Cited

OTHER PUBLICATIONS

Luongo et al., (2014) The sonic hedgehog-induced type 3 deiodinase facilitates tumorigenesis of basal cell carcinoma by reducing Gli2 inactivation. Endocrinology 155(6): 2077-2088.
Mahboobi et al., (1999) Homoarcyriaflavin: synthesis of ring-expanded arcyriaflavin analogues. The Journal of Organic Chemistry 64(22): 8130-8137.
Mahboobi et al., (2000) Synthesis of bis (indolylmaleimide) macrocycles. Journal of Heterocyclic Chemistry 37(2): 307-329.
Mahboobi et al., (2006) 3-Bromo-4-(1H-3-indolyl)-2, 5-dihydro-1H-2, 5-pyrroledione derivatives as new lead compounds for antibacterially active substances. European Journal of Medicinal Chemistry 41(2): 176-191.
Manna & Mugesh (2010) A Chemical Model for the Inner-Ring Deiodination of Thyroxine by Iodothyronine Deiodinase. Angew Chem Int Ed 49: 9246-9249.
Manna & Mugesh (2011) Deiodination of thyroid hormones by iodothyronine deiodinase mimics: does an increase in the reactivity alter the regioselectivity?. Journal of the American Chemical Society 133(26): 9980-9983.
Manna & Mugesh (2012) Regioselective deiodination of thyroxine by iodothyronine deiodinase mimics: an unusual mechanistic pathway involving cooperative chalcogen and halogen bonding. Journal of the American Chemical Society 134(9): 4269-4279.
Manni et al., (2012) 3-Iodothyronamine: a modulator of the hypothalamus-pancreas-thyroid axes in mice. British Journal of Pharmacology 166(2): 650-658.
Marculescu et al., (2014) Aryloxymaleimides for cysteine modification, disulfide bridging and the dual functionalization of disulfide bonds. Chem Commun 50(54): 7139-7142.
Martin et al., (1961) 4-(2-Cyano-3-maleimidyl) arylamines and related colored compounds. The Journal of Organic Chemistry 26(6): 2032-2037.
Muus et al., (2010) Development of antiproliferative phenylmaleimides that activate the unfolded protein response. Bioorganic & Medicinal Chemistry 18(12): 4535-4541.
Nauman et al., (2003) The concentration of thyroid hormones and activities of iodothyronine deiodinases are altered in human brain gliomas. Folia neuropathologica/Association of Polish Neuropathologists and Medical Research Centre, Polish Academy of Sciences 42(2): 67-73.
Ocasio & Scanlan (2005) Clinical prospects for new thyroid hormone analogues. Current Opinion in Endocrinology, Diabetes and Obesity 12(5): 363-370.
Okun et al., (2010) Toll-like receptor 3 inhibits memory retention and constrains adult hippocampal neurogenesis. Proceedings of the National Academy of Sciences 107(35): 15625-15630.
Patel & Dholakiya (2012) Synthesis of 1-(4-((E)-3-arylacryloyl) phenyl)-3, 4-dibromo-1H-pyrrole-2, 5-diones and screening for anti-Candida and antituberculosis activity. Medicinal Chemistry Research 21(8): 1977-1983.
Patel et al., (2012) Silica sulfuric acid-catalyzed Claisen-Schmidt condensation of 1, 3, 4 trisubstituted pyrrole 2, 5 dione to chalcones. Research on Chemical Intermediates 38(9): 2371-2381.
Preparation of some N-substituted adducts from aromatic nitro amines. Azerbaidzhanskii Khimicheskii Zhumal (2008), (2), pp. 180-186 in Russian CODEN: AZKZAU ISSN:0005-253, Nagiev, Ya. M et al, Feb. 1, 199, Registry No. 131692-85-8.
Routier et al., (2002) First synthesis of symmetrical and non-symmetrical aza indolocarbazoles derivatives. Tetrahedron Letters 43(14): 2561-2564.
Routier et al., (2002) Synthesis and biological evaluation of 7-azaindolocarbazoles. Tetrahedron 58(33): 6621-6630.
Rush et al., (2006) Acute and longer-term outcomes in depressed outpatients requiring one or several treatment steps: a STAR* D report. American Journal of Psychiatry 163(11): 1905-1917.
Samuelsen & Meredith (2011) Oxytocin antagonist disrupts male mouse medial amygdala response to chemical-communication signals. Neuroscience 180: 96-104.
Sanders et al., (1999) Cloning and Characterization of Type III Iodothyronine Deiodinase from the Fish Oreochromis niloticus 1. Endocrinology 140(8): 3666-3673.
Santarelli et al., (2003) Requirement of hippocampal neurogenesis for the behavioral effects of antidepressants. Science 301(5634): 805-809.
Schumacher et al., (2014) Next generation maleimides enable the controlled assembly of antibody—drug conjugates via native disulfide bond bridging. Organic & Biomolecular Chemistry 12(37): 7261-7269.
Sheherbakov et al., (1992) Organotin derivatives of some N-(2,2'-dichloromaleoyl)-protected amoni acids and dipeptides. Metalloorganicheskaya Khimiya 5(3): 632-642.
Shorunov et al., (2006) A convenient synthesis of 3, 4-diaryl (hetaryl)-substituted maleimides and maleic anhydrides. Russian Journal of Organic Chemistry 42(10): 1490-1497.
Smith et al., (2010) Protein modification, bioconjugation, and disulfide bridging using bromomaleimides. Journal of the American Chemical Society 132(6): 1960-1965.
Stoedter et al., (2015) Strong induction of iodothyronine deiodinases by chemotherapeutic selenocompounds. Metallomics 7(2): 347-354.
Tsuji et al., (2013) Enantioselective binding of chiral 1, 14-dimethyl [5] helicene—spermine ligands with B-and Z-DNA. Bioorganic & Medicinal Chemistry 21(19): 6063-6068.
Ubhi et al., (2010) Neurodegeneration in a transgenic mouse model of multiple system atrophy is associated with altered expression of oligodendroglial-derived neurotrophic factors. The Journal of Neuroscience 30(18): 6236-6246.
Waghray & Dehaen (2013) A Fragment Based Approach toward Thia [n] helicenes. Organic Letters 15(12): 2910-2913.
Wang & Liu (2014) Synthesis and cytotoxic activities of a series of novel N-methyl-bisindolylmaleimide amide derivatives. Journal of Asian Natural Products Research 16(3): 296-303.
Wang et al., (2001) Practical synthesis of the rebeccamycin aglycone and related analogs by oxidative cyclization of bisindolylmaleimides with a Wacker-type catalytic system. Tetrahedron Letters 42(51): 8935-8937.
Wang et al., (2005) Highly convergent synthesis of a rebeccamycin analog with benzothioeno (2, 3-a) pyrrolo (3, 4-c) carbazole as the aglycone. Tetrahedron Letters 46(6): 907-910.
Wei et al., (2012) From distributed resources to limited slots in multiple-item working memory: a spiking network model with normalization. The Journal of Neuroscience 32(33): 11228-11240.
Wilson et al., (2006) Enantioselective synthesis of a PKC inhibitor via catalytic CH bond activation. Organic Letters 8(8) 1745-1747.
Yang et al., (2012) Tramadol pretreatment enhances ketamine-induced antidepressant effects and increases mammalian target of rapamycin in rat hippocampus and prefrontal cortex. BioMed Research International, 2012.
Yang et al., (2013) Acute administration of ketamine in rats increases hippocampal BDNF and mTOR levels during forced swimming test. Upsala Journal of Medical Sciences 118(1): 3-8.
Yao et al., (1999) Mice deficient in interleukin-1β converting enzyme resist anorexia induced by central lipopolysaccharide. American Journal of Physiology-Regulatory, Integrative and Comparative Physiology 277(5): R1435-R1443.
Yoshida et al., (2002) New synthetic route to granulatimide and its structural analogues. Chemical and Pharmaceutical Bulletin 50(6): 872-876.
Yoshida et al., (2003) Synthesis of granulatimide positional analogues. Chemical and Pharmaceutical Bulletin 51(2): 209-214.
Yoshihara & Scanlan (2003) Selective thyroid hormone receptor modulators. Current Topics in Medicinal Chemistry 3 (14): 1601-1616.
Yunes et al., (2008) Antiproliferative effects of a series of cyclic imides on primary endothelial cells and a leukemia cell line. Zeitschrift für Naturforschung C 63(9-10): 675-680.
Zembower et al., (1999) Indolocarbazole poisons of human topoisomerase I: regioisomeric analogues of ED-110. Bioorganic & Medicinal Chemistry Letters 9(2): 145-150.
Zang et al., (2004) Ruthenium complexes as protein kinase inhibitors. Organic Letters 6(4): 521-523.

(56) References Cited

OTHER PUBLICATIONS

Zhang et al., (2010) Effects of neonatal flutamide treatment on hippocampal neurogenesis and synaptogenesis correlate with depression-like behaviors in preadolescent male rats. Neuroscience 169(1): 544-554.
Aan Het Rot et al., (2012) Ketamine for depression: where do we go from here?. Biological Psychiatry 72(7): 537-547.
Ambrogi et al., (2013) Atropisomers of arylmaleimides: stereodynamics and absolute configuration. The Journal of Organic Chemistry 78(8): 3709-3719.
Augustin et al., (1972) Dicarboxylic acid imides Wissenschaftliche Zeitschrift-Martin-Luther-Universitaet Halle-Wittenberg, Mathematisch—Naturwissenschaftliche Reihe 21(2): 137-8 In German, CODEN: WMHMAP ISSN: 0138-1504, Nov. 16, 1984, Registry No. 37461-23-7.
Awuah & Capretta (2011) Development of Methods for the Synthesis of Libraries of Substituted Maleimides and α, β-Unsaturated-γ-butyrolactams. The Journal of Organic Chemistry 76(9): 3122-3130.
Balasubramanian et al., (2004) Design and Synthesis of a Fluoroindolocarbazole Series as Selective Topoisomerase I Active Agents. Discovery of Water-Soluble 3, 9-Difluoro-12, 13-dihydro-13-[6-amino-β-d-glucopyranosyl]-5 H, 13 H-benzo [b]-thienyl [2, 3-a] pyrrolo [3, 4-c] carbazole-5, 7 (6 H)-dione (BMS-251873) with Curative Antitumor Activity against Prostate Carcinoma Xenograft Tumor Model §. Journal of Medicinal Chemistry 47(7): 1609-1612.
Bartlett & Nelson (2004) Evaluation of alternative approaches for the synthesis of macrocyclic bisindolylmaleimides. Organic & Biomolecular Chemistry 2(19): 2874-2883.
Beaufort et al., (2014) Ovarian cancer cell line panel (OCCP): clinical importance of in vitro morphological subtypes. PLoS One 9(9): e103988; 16 pages.
Becker et al., (1997) The Type 2 and Type 3 Iodothyronine Deiodinases Play Important Roles in Coordinating Development in Rana catesbeiana Tadpoles 1. Endocrinology 138(7): 2989-2997.
Bianco et al., (2002) Biochemistry, cellular and molecular biology, and physiological roles of the iodothyronine selenodeiodinases. Endocrine Reviews 23(1): 38-89.
Borchhardt & Andricopulo (2009) CoMFA and CoMSIA 3D QSAR models for a series of cyclic imides with analgesic activity. Medicinal Chemistry 5(1): 66-73.
Bourderioux et al., (2007) Synthesis of benzo analogs of oxoarcyriaflavins and caulersine. Tetrahedron 63(38): 9465-9475.
Brenet et al., (2013) 3, 3'-Diiodo-BINOL-Fused Maleimides as Chiral Hypervalent Iodine (III) Organocatalysts. European Journal of Organic Chemistry 2013(36): 8094-8096.
Brenet et al., (2013) BINOL-Fused Maleimides—A New Class of C2-Symmetric Chiral Imides. European Journal of Organic Chemistry 2013(6): 1041-1045.
Budke et al., (2012) An optimized RAD51 inhibitor that disrupts homologous recombination without requiring Michael acceptor reactivity. Journal of Medicinal Chemistry 56(1): 254-263.
Castañeda et al., (2013) A mild synthesis of N-functionalised bromomaleimides, thiomaleimides and bromopyridazinediones. Tetrahedron Letters 54(27): 3493-3495.
Castañeda et al., (2013) Acid-cleavable thiomaleamic acid linker for homogeneous antibody—drug conjugation. Chemical Communications 49(74): 8187-8189.
Chan et al., (2012) Inhibition of glycogen synthase kinase-3 attenuates psychotomimetic effects of ketamine. Schizophrenia Research 136(1):96-103.
Cheng & Lee (2008) Total synthesis of (±)-camphorataimides and (±)-himanimides by NaBH 4/Ni (OAc) 2 or Zn/AcOH stereoselective reduction. Tetrahedron 64(19): 4347-4353.
Choi et al., (1998) Revised structures of N-substituted dibrominated pyrrole derivatives and their polymeric products. Termaleimide models with low optical band gaps. The Journal of Organic Chemistry 63(8) 2646-2655.
Cooper-Kazaz & Lerer (2008) Efficacy and safety of triiodothyronine supplementation in patients with major depressive disorder treated with specific serotonin reuptake inhibitors. International Journal of Neuropsychopharmacology 11(5): 685-699.
Cruchter et al., (2013) Strain-Promoted Azide-Alkyne Cycloaddition with Ruthenium (II)—Azido Complexes. Chemistry—A European Journal 19(49): 16682-16689.
David et al., (2007) Efficacy of the MCHR1 antagonist N-[3-(1-{[4-(3, 4-difluorophenoxy) phenyl] methyl}(4-piperidyl))-4-methylphenyl]-2-methylpropanamide (SNAP 94847) in mouse models of anxiety and depression following acute and chronic administration is independent of hippocampal neurogenesis. Journal of Pharmacology and Experimental Therapeutics 321(1): 237-248.
Dentice & Salvatore (2011) Local impact of thyroid hormone inactivation. Journal of Endocrinology 209(3): 273-282.
Dentice et al., (2013) Type 3 deiodinase and solid tumors: an intriguing pair. Expert Opinion on Therapeutic Targets 17 (11): 1369-1379.
Dolomatov et al., (1990) New approach to the directed synthesis of 2,3-dichloromaleimide-type biocides. Zhurnal Vsesoyuznogo Khimicheskogo Obshchestva im. D. I. Mendeleeva 35(2): 271-272.
Domcke et al., (2013) Evaluating cell lines as tumour models by comparison of genomic profiles. Nat Commun 4: 2126; 10 pages.
Du Mont et al., (2001) Reactions of organoselenenyl iodides with thiouracil drugs: an enzyme mimetic study on the inhibition of iodothyronine deiodinase. Angewandte Chemie International Edition 40(13): 2486-2489.
Dubernet et al., (2005) Synthesis of substituted bis (heteroaryl) maleimides. Tetrahedron 61(19): 4585-4593.
Duncan et al., (2013) Concomitant BDNF and sleep slow wave changes indicate ketamine-induced plasticity in major depressive disorder. International Journal of Neuropsychopharmacology 16(2): 301-311.
Eitan et al., (2010) The thyroid hormone, triiodothyronine, enhances fluoxetine-induced neurogenesis in rats: possible role in antidepressant-augmenting properties. International Journal of Neuropsychopharmacology 13(5): 553-561.
El Yahyaoui et al., (2007) Convenient synthesis of photochromic symmetrical or unsymmetrical bis (heteroaryl) maleimides via the Suzuki—Miyaura cross-coupling reaction. Tetrahedron 63(38): 9482-9487.
Fickentscher & Kohler (1976) Teratogenicity and embryotoxicity of some maleinimides. Archives of Toxicology 37(1): 15-21.
Garber et al., (2001) A new synthetic class A amphipathic peptide analogue protects mice from diet-induced atherosclerosis. Journal of Lipid Research 42(4): 545-552.
Gerasimova et al., (1984) Polarography of haloorganic compounds. XVII. Polarographic study of N-substituted 3,4-dichloro-2,5-dioxo-3-pyrrolines Zhurnal Obshchei Khimii (19830131), 53(1): 185-8, CODEN: ZOKHA4 ISSN: 0044-460X, Nov. 16, 1984, Registry No. 84954-18-7.
Germain et al., (2005) Insights into the role of deiodinases from studies of genetically modified animals. Thyroid 15(8): 905-916.
Green (1968) Inhibition of Thyroidal Iodotyrosine Deiodination byTyrosine Analogues. Endocrinology 83(2): 336-347.
Hernandez et al., (2010) Type 3 deiodinase deficiency causes spatial and temporal alterations in brain T3 signaling that are dissociated from serum thyroid hormone levels. Endocrinology 151(11): 5550-5558.
Huang et al., (2011) The thyroid hormone degrading type 3 deiodinase is the primary deiodinase active in murine epidermis. Thyroid 21(11): 1263-1268.
Jones et al., (2012) Polymeric dibromomaleimides as extremely efficient disulfide bridging bioconjugation and pegylation agents. Journal of the American Chemical Society 134(3): 1847-1852.
Joyce et al., (1987) Synthesis of the aromatic and monosaccharide moieties of staurosporine. The Journal of Organic Chemistry 52(7): 1177-1185.
Kaneko et al., (1985) Two synthetic approaches to rebeccamycin. Tetrahedron Letters 26(34): 4015-4018.
Karabacak et al., (2008) FT-IR, FT-Raman, NMR spectra, and molecular structure investigation of 2, 3-dibromo-N-methylmaleimide: A combined experimental and theoretical study. Journal of Molecular Structure 892(1): 125-131.

(56) References Cited

OTHER PUBLICATIONS

Katoh et al., (2005) Structure-activity relationship of N-methyl-bisindolylmaleimide derivatives as cell death inhibitors. Bioorganic & Medicinal Chemistry Letters 15(12): 3109-3113.

Kaźmierczak (2001) Circular dichroism of some optically active 2,3-dichloromaleimides. Enantiomer 6(4): 251-258.

Khotinsky & Pictet (1904) Ueber Bromderivate der Pyrrol-α-carbonsaure and der N-Methylpynrol-α-carbonsaure. Berichte der Deutschen Chemischen Gesellschaft 37(3): 2798-2802.

Křupková et al., (2013) 4-Chloro-2-fluoro-5-nitrobenzoic acid as a possible building block for solid-phase synthesis of various heterocyclic scaffolds. ACS Combinatorial Science 15(1): 20-28.

Kul'nevich et al., (1982) Oxidation of 1-(4-nitrophenyl)-2-formylpyrrole. Chemistry of Heterocyclic Compounds 18(4): 375-379.

Lakatosh et al., (2003) Synthesis of 6 H-pyrrolo [3', 4': 2, 3][1, 4] diazepino [6, 7, 1-hi] indole-8, 10 (7 H, 9 H)-diones using 3-bromo-4-(indol-1-yl) maleimide scaffold. Organic & Biomolecular Chemistry 1(5): 826-833.

Lakatosh et al., (2006) Introduction of pharmacophore groups into bis (indol-1-yl) maleimides and 6H-pyrrolo [3, 4: 2, 3][1, 4] diazepino [6, 7, 1-hi]-indolo-8, 10 (7H, 9H)-diones. Pharmaceutical Chemistry Journal 40(8): 435-440.

Lefoix et al., (2008) Novel 5-azaindolocarbazoles as cytotoxic agents and Chk1 inhibitors. Bioorganic & Medicinal Chemistry 16(9): 5303-5321.

Dentice et al., (2007) Sonic hedgehog-induced type 3 deiodinase blocks thyroid hormone action enhancing proliferation of normal and malignant keratinocytes. Proc Natl Acad Sci U S A 104(36): 14466-14471.

Dentice et al., (2012) β-Catenin regulates deiodinase levels and thyroid hormone signaling in colon cancer cells. Gastroenterology 143(4): 1037-1047 with supplemental data.

\* cited by examiner

TYPE III DEIODINASE INHIBITORS AND USES THEREOF

CROSS REFERENCE TO RELATED APPLICATIONS

This application is a Continuation of U.S. application Ser. No. 15/126,023, filed on Sep. 14, 2016, which is a 35 U.S.C. 371 National Phase Entry Application from PCT/IL2015/050277, filed on Mar. 16, 2015, which claims the benefit of U.S. Provisional Application Nos. 61/953,846 filed on Mar. 16, 2014 and 62/097,142 filed on Dec. 29, 2014, the disclosure of each of which are incorporated herein in their entirety by reference.

FIELD OF THE INVENTION

The present invention relates to compounds that inhibit the activity of Type III deiodinase (DIO3) and to the use of DIO3 inhibitors for treating or preventing depression, depression associated with other disorders or conditions, and cancer.

BACKGROUND OF THE INVENTION

Mood disorders are among the most prevalent forms of mental illness. Severe forms of mental illness affect 2%-5% of the US population and up to 20% of the population suffers from milder forms of the illness. The economic costs to society and personal costs to individuals and families are enormous.

Depressive syndromes occur in the context of a vast number of mental and medical illnesses. Depression is a central feature of major depressive disorder and bipolar disorder. Anxiety disorders, such as post-traumatic stress disorder (PTSD), obsessive-compulsive disorder, panic disorder, social phobia, and generalized anxiety disorder, are often accompanied by depression. Alcohol and other substance abuse or dependence may also co-exist with depression. Research shows that mood disorders and substance abuse commonly occur together. Depression also may occur with other serious medical illnesses such as heart disease, stroke, cancer, HIV/AIDS, diabetes, and Parkinson's disease.

People who have depression along with another medical illness tend to have more difficulty adapting to their medical condition, and more medical costs than those who do not have co-existing depression. Treating the depression can also help improve the outcome of treating the co-occurring illness.

There are several forms of depressive disorders. Major depressive disorder, or major depression, is characterized by a combination of symptoms that interfere with a person's ability to work, sleep, study, eat, and enjoy once-pleasurable activities. Major depression is disabling and prevents a person from functioning normally. Some people may experience only a single episode within their lifetime, but more often a person may have multiple episodes.

Currently available pharmacological treatments for major depression are severely limited in their efficacy (Rush A J et al. *Am J Psychiatry* 2006; 163, 1905-1917). No more than a third of patients achieve remission on standard treatment and at least a third remains ill after a year or more of serial treatments.

The hormone L-3,3',5,5',-tetraiodothyronine (L-thyroxine or T4) is a product of the thyroid gland. Although thyroxine (tetraiodothyronine; T4) is the principal secretory product of the vertebrate thyroid, it's essential metabolic and developmental effects are primarily mediated by 3,3',5-triiodothyronine (T3), which is produced from the prohormone by 5'-deiodination.

T4 is converted by one of three selenium-containing enzymes (deiodinases) into either the active hormone L-3, 3',5,-triiodothyronine (T3), the inactive T3 competitive product L-3,3',5'-triiodothyronine referred to as reverse T3 (rT3) or, indirectly (by first being converted to T3) to the deactivated L-3,3'-diiodothyronine (3,3'-T2). Type I iodothyronine deiodinase (DIO1), a thiol-requiring propyl-thiouracil-sensitive oxidoreductase, is found mainly in liver and kidney and catalyzes conversion of T3 and rT3 by deiodination of the phenolic ring 5' position iodine to form T3 or deiodination of the tyrosyl ring 5 position iodine to form rT3. Type II deiodinase (DIO2) is responsible for intracellular deiodination and its activity is limited to phenolic ring 5' position deiodination to form T3 from T4. While the activity of DIO2 is similar to that of DIO1, DIO2 is primarily found in the thyroid, pituitary gland, brain, brown fat and testis. Type III deiodinase (DIO3) activity is limited to inner ring deiodination of T4 and T3 to the inactive rT3 and T2 products, respectively. DIO3 is primarily found in the brain, and can further be found in fetal tissues, placenta, skin and adipose tissue. DIO3 is not found in the heart or in bones. These reactions are illustrated in FIG. 1.

T3 is metabolically active and stimulates production of cellular energy, and generally is an activator of tissues and organs. T3 acts by diffusing into cells, where it interacts with a cellular protein which transports the T3 to the cellular nucleus. T3 then acts by stimulating gene transcription to produce messenger ribonucleic acids (mRNA) of certain genes. Translation of the T3-induced mRNA produces cellular proteins that promote cellular activation. In contrast, rT3 has opposing effects, at least partially by inhibiting the action of T3, by way of competitively inhibiting T3 nuclear receptors in cells.

The thyroid hormone, triiodothyronine (T3), is widely used to augment antidepressant action in depressed patients who have not responded to treatment with conventional antidepressants. While T3 is rarely used clinically as a monotherapy, the inventors of the present invention and co-workers have shown that chronic administration of the hormone has a dose dependent, antidepressant-like effect using screening tests including the forced swim test (FST), tail suspension test (TST) and novelty suppressed feeding test (NSFT) in mice (Lifschytz T et al. *J. Pharmacol. Exp. Ther.* 2011; 337, 494-502). Using in vivo microdialysis it has been also shown that chronic administration of T3 enhances serotonergic neurotransmission in rat frontal cortex and hypothalamus by functional desensitization of presynaptic 5-HT1A and 5-HT1B receptors which inhibit serotonin release (Lifschytz T et al. *Curr. Drug Targets* 2006; 7, 203-210). Moreover, when administered concurrently with fluoxetine (an anti-depressant also known by the tradename Prozac), T3 enhances neurogenesis in the rat hippocampus over and above the effect of fluoxetine alone (Eitan, R et al. *Int J. Neuropsychopharmacol.* 2010; 13, 553-561).

Although it has been suggested that administration of T3 can overcome depression symptoms it is not feasible to use T3 or synthetic analogs thereof as a first line treatment for depression because the hormone has significant effects on heart rate and bone density that limit long term use. Moreover, it has been recently shown that in mice the antidepressant effects of T3 are mediated by the same thyroid receptor subtypes responsible for T3 effects on heart rate and bone density (Lifschytz et al. 2011, ibid).

High expression of DIO3 with a crucial role in sustaining cell proliferation has been documented at sites of local inflammation, in the infarcted heart, during liver regeneration and in peripheral nerves after injury. DIO3 has also been shown to be re-expressed in various neoplastic tissues while remaining silent in the normal counterpart tissues.

Elevated DIO3 mRNA and activity levels were shown in a variety of cancer cell lines including endometrium, neuroblastoma, colon, liver, basal cell carcinomas and breast cancer (Dentice M et al., *Expert Opin Ther Targets*, 2013; 17(11), 1369-79; Luongo C et al., *Endocrinology* 2014; 155(6), 2077-88) and in a number of human brain tumors (Nauman P et al., *Folia Neuropathol* 2004; 42(2), 67-73.). DIO3 expression has been found to be under the control of several signaling molecules and pathways that are major driving forces of cellular division, including HIF-1α, TGF and the Wnt-β-catenin pathway (Dentice M et al., *J Endocrinol*, 2011; 209(3), 273-82). It is thus proposed that DIO3 is under the control of an intricate circuit of signaling pathways that play a central role in the oncogenic process.

Elevating T3 concentration or the ratio of active T3 to non-active rT3 for treating various disorders has been suggested.

For example, PCT Patent Application Publication No. WO 03/099105 discloses methods for diagnosis and treatment of several disorders characterized by elevated serum ratio of rT3 to T3 defined as human dormancy syndrome. The treatment of human dormancy syndrome is directed toward increasing functional T3 levels or decreasing the inactive rT3 levels, or both, using pharmaceutical and/or behavioral methods, particularly via the modulation of type I deiodinase activity. Exemplified therein is the effect of T3 administration of several human dormancy syndrome disorders, depression being listed among the many other of the manifestations of this syndrome.

PCT Patent Application Publication No. WO 2006/028835 discloses the use of thyroid hormone conversion inhibitors to treat hyperproliferative skin disorders, preferably their use in topical admixtures. Particularly, the invention discloses the use of deiodinase inhibitors such as an iodinated contrast agent, e.g., iopanoic acid (IOP) and/or its analogs.

PCT Patent Application Publication No. WO 2008/140713 discloses methods for regulating the levels of type 3 iodothyronine deiodinase (DIO3) and or thyroid hormone in cancerous and pre-cancerous cells and related compositions and kits. siRNA and antisense oligonucleotides are suggested as DIO3 inhibitors.

PCT Patent Application Publication No. WO 2009/015366 discloses methods of treating conditions associated with hyperproliferation of cells, such as hirsutism, hypertrichosis, scar formation, ocular hyperproliferative disease, and pulmonary hyperproliferative disease, comprising administering thyroid hormone conversion inhibitor. In particular embodiments, the thyroid hormone conversion inhibitor is selected from the group consisting of iopanoic acid (IOP), ipodate, and propranolol.

Stoedter et al., published after the priority of the present invention, describe the effect of several selenocompounds containing a methyl- or benzyl-imidoselenocarbamate backbone on DIO expression in cancerous cells in vitro. A deferential effect was observed with the compounds examined, highlighting that these selenocompounds may constitute interesting pharmacological compounds for modifying DIO expression, potentially affecting the balance between cell differentiation and proliferation (Stoedter et al., *Metallomics* 2015; 7(2), 347-54).

U.S. Pat. No. 8,304,401 discloses methods for decreasing fat mass, increasing energy expenditure, increasing resistance to obesity, and lowering blood glucose levels in a subject with an agent that inhibits the expression or activity of type III deiodinase (DIO3). The inhibiting agent is an antisense, siRNA, siRNA-like, or ribozyme molecule and the agents of the invention are useful in treating diabetes and obesity.

An inventor of the present invention and co-workers have extensively studied the deiodination of thyroxine and related compounds, and have recently reported the first examples of synthetic compounds that functionally mimic DIO3 activity (FIG. 2) (Manna and Mugesh, *Angew. Chem. Int. Ed.* 2010; 49, 9246-9249; Manna and Mugesh, *J. Am. Chem. Soc.*, 2011, 133, 9980-9983; Manna and Mugesh, *J. Am. Chem. Soc.* 2012; 134, 4269-4279).

To date, no effective specific inhibitors for Type III deiodinase (DIO3) are used as therapeutic compounds. DIO3 specific inhibitors could be efficient in treating diseases in which attenuating the expression and/or activity of this enzyme is desired, including depression in the context of major depressive disorder and bipolar disorder and depression associated with other diseases or conditions, and cancer.

There is an ongoing need for and it would be highly advantageous to have drugs which would inhibit cancerous states. Further, there is a critical and ongoing need for drugs for treating neuropsychiatric disorders and depression associated conditions that are specific and have minimal deleterious side effects.

SUMMARY OF THE INVENTION

The present invention relates to compounds that inhibit the activity of Type III deiodinase (DIO3). The present invention further relates to methods for treating or preventing undesired conditions in which attenuating the activity of DIO3 have a beneficial effect, particularly by administering the compounds of the present invention.

The present invention is based in part on a novel system for identifying small molecules capable of specifically inhibiting DIO3, utilizing synthetic compounds that functionally mimic the DIO3 activity. An inventor of the present invention and co-workers have previously reported that naphthyl-based compounds having two selenols in the peri-positions exhibit deiodinase activity and thus act as DIO3 mimics (Manna and Mugesh 2010, ibid; Manna and Mugesh 2011 ibid; Manna and Mugesh 2012, ibid). These compounds (See, e.g. compound A, FIG. 3) have been shown to behave similarly to DIO3 with respect to deiodination. Namely, the compounds remove iodine selectively from the tyrosyl ring of T4 or T3 and produce rT3 and 3,3'-T2, respectively (FIG. 2).

In view of those findings, DIO3 mimics were used as powerful tools for the design of compounds that specifically inhibit the DIO3 enzyme and thus are useful in the treatment of conditions where attenuation of DIO3 expression or activity provides a beneficial outcome, including central nervous system (CNS) diseases, depression and depression associated with other conditions and in the treatment of conditions implicated with undesired expression or activity of DIO3, for example diseases associated with cell overproliferation, particularly cancer.

The compounds so identified are useful in inhibiting DIO3 activity.

Without being bound by any theory or mechanism of action, the compounds of the invention increase the endogenous amounts of T3 by inhibiting DIO3 activity, which catalyzes conversion of the active hormone 3,5,3'-triiodothyronine (T3) to the inactive metabolite T2.

The teachings of the present invention are advantageous over the hitherto known direct use of T3 as antidepressant, as chronic administration of T3 is associated with deleterious side effects, including enhancement of bone depletion, muscle weakness and tachycardia. To the contrary, the selective inhibition of DIO3, known to be primarily active in the brain, results in the desired effect of alleviating depression and associated conditions while having a minor effect on the heart, bones and muscles. DIO3 has also been correlated with hyperproliferative states and solid tumors, and thus specific inhibition of DIO3 is advantageous for treating these conditions.

It is contemplated that the ability of a compound to simultaneously react with both selenol moieties of the DIO3 mimic provides for its specific inhibition of DIO3. Based on this, the applicants designed and synthesized maleimide-based compounds of formula (I), which are linked to a phenylcarboxylic acid (e.g., p-benzoic acid or iopanoic acid) moiety (as exemplified in Formula II), or to a side chain or an amino acid, e.g., tyrosine (as exemplified in Formula III). The two simultaneous nucleophilic attacks of the selenol moieties at the carbons adjacent to the carbonyl groups of the maleimide derivatives are expected to block the selenium centers by forming a stable adduct, thus leading to inhibition of deiodinase activity. In some embodiments, the compounds were advantageously designed to be water soluble.

Thus, according to one aspect, the present invention provides a compound having the general formula I:

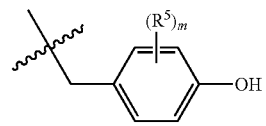

(I)

wherein

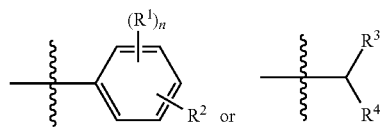

A is $R^1$ is independently at each occurrence a halogen, OH, $NO_2$ or $N(R)_2$ wherein each R is independently H or a $C_1$-$C_6$ alkyl;

$R^2$ is COOH, OH, $NO_2$, $N(R)_2$ or a linear or branched $C_1$-$C_6$ alkyl substituted with at least one group selected from the group consisting of COOH, halogen, OH, $NO_2$, and $N(R)_2$;

$R^3$ is H or COOH;

$R^4$ is iodophenyl, heterocyclyl, heteroaryl, or the side chain of an amino acid selected from the group consisting of tyrosine, 3,4-dihydroxyphenylalanine (DOPA), iodotyrosine, aspartic acid, valine, leucine, isoleucine, methionine, tryptophan, threonine, asparagine, glutamine, cysteine, proline, arginine, histidine, lysine, glutamic acid; or $R^4$ is represented by the structure:

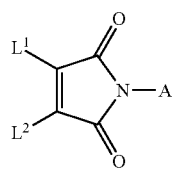

wherein $R^5$ is independently at each occurrence OH, halogen, $NO_2$ or $N(R)_2$ and m is 0, 1, 2, 3 or 4;

$L^1$ and $L^2$ are each a leaving group selected from a halogen and a sulfonate;

n is 1, 2, 3 or 4;

and salts thereof.

In one embodiment, the compound of formula (I) is a phenylcarboxylic acid derivative (e.g., p-benzoic acid derivative or iopanoic acid derivative), represented by the structure of formula (II):

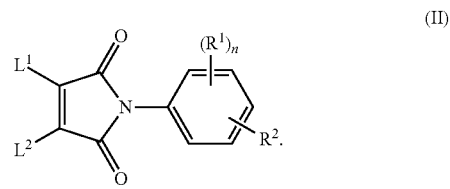

(II)

In some embodiments, n=0 in compound (II), and $R^1$ does not exist. In other embodiments, however, the phenyl ring is substituted with one or more halogens, OH, $NO_2$ or $N(R)_2$ wherein each R is independently H or a $C_1$-$C_6$ alkyl. In accordance with this embodiment, n in formula (II) is 1, 2, 3 or 4, preferably 2 or 3. In one embodiment of formula (II), $R^1$ is halogen, preferably a bromine or iodine. In another embodiment of formula (II), $R^1$ is OH. In another embodiment of formula (II), n is 2 or 3, and $R^1$ is iodine. Each possibility represents a separate embodiment of the present invention.

In one embodiment of formula (II), $R^2$ is COOH, which can be in the ortho, meta or para position, and preferably in the para position. In accordance with this embodiment, compound (II) is a benzoic acid derivative, preferably a p-benzoic acid derivative. In another embodiment of formula (II), $R^2$ is OH (i.e., the compound is a phenol derivative).

The OH can be positioned anywhere on the ring. In another embodiment of formula (II), $R^2$ is a linear or branched $C_1$-$C_6$ alkyl substituted with a COOH at any location. In one currently preferred embodiment, $R^2$ is —$CH_2CH(COOH)CH_2CH_3$. In accordance with this embodiment, the compound is derived from iopanoic acid. Each possibility represents a separate embodiment of the present invention.

In another embodiment, the compound of formula (I) is represented by the structure of formula (III):

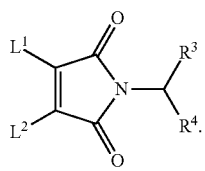

(III)

In one embodiment of formula (III), $R^4$ is the side chain of tyrosine. In another embodiment of formula (III), $R^4$ is the side chain of 3,4-dihydroxyphenylalanine (also designated 3-hydroxy tyrosine or DOPA). In another embodiment of formula (III), $R^4$ is the side chain of 3,5-diiodotyrosine. In another embodiment, $R^4$ is represented by the structure:

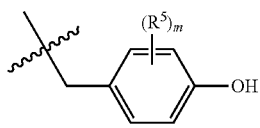

wherein $R^5$ is OH, halogen, $NO_2$ or $N(R)_2$ and m is 0, 1, 2, 3 or 4.

In some embodiments of formula (III), m=0 and $R^5$ does not exist. In other embodiments, however, the phenol ring is substituted with one or more hydroxyls (OH), halogens (preferably bromine or iodine), $NO_2$ and/or $N(R)_2$. In accordance with this embodiment, m in formula (I) is 1, 2, 3 or 4, preferably 1, 2 or 3. Each possibility represents a separate embodiment of the present invention.

In another embodiment of formula (III), $R^4$ is iodophenyl which is selected from 2-iodophenyl, 3-iodophenyl and 4-iodophenyl. In another embodiment, $R^4$ is tetrahydrofuryl. Each possibility represents a separate embodiment of the present invention.

In another embodiment of formula (III), $R^4$ in formula (I) is the side chain of aspartic acid, i.e., —$CH_2$—COOH. In another embodiment, $R^4$ is the side chain of an amino acid selected from the group consisting of valine, leucine, isoleucine, methionine, tryptophan, threonine, asparagine, glutamine, cysteine, proline, arginine, histidine, lysine and glutamic acid.

In another embodiment, the compound is an ethyl diiodophenol, iodobenzyl or tetrahydrofuryl derivative, represented by the structure of formula (III).

The $L^1$ and $L^2$ substituents in Formula (I) or (II) are leaving groups selected from a halogen (preferably Br or I) or a sulfonate represented by the structure $OSO_2R'$ wherein R' is an alkyl or aryl (e.g., OAc (0-acetate), OTs (tosylate), OMs (mesylate), OTf (triflate)). Preferred $L^1$ and $L^2$ substituents are halogens, especially bromine.

According to another aspect, the present invention provides a pharmaceutical composition comprising the compounds of the present invention, which are represented by Formula (I) or (II), e.g., compounds 3, 5, 6, 7, 8, 9, 10, 11 or 12, further comprising a pharmaceutically acceptable diluent or carrier.

According to yet an additional aspect, the present invention provides a method for treating or preventing depression, the method comprises administering to a subject in need thereof a therapeutically effective amount of a compound that inhibits the activity of Type III deiodinase (DIO3) thereby treating or preventing depression.

According to certain exemplary embodiments, the method comprises administering to a subject in need thereof a therapeutically effective amount of at least one compound of the invention as described herein that inhibits the activity of Type III deiodinase (DIO3) or a pharmaceutical composition comprising same, thereby treating or preventing depression.

According to further aspect, the present invention provides a compound that inhibits the activity of Type III deiodinase (DIO3) or a pharmaceutical composition comprising same for use in the treatment or prevention of depression or a depression associated disease or disorder, wherein said compound inhibits the activity of Type III deiodinase (DIO3).

According to certain exemplary embodiments, the compound that inhibits the activity of Type III deiodinase (DIO3) is a compound according to the teachings of the present invention.

According to some embodiments, the depression is associated with a condition selected from the group consisting of major depressive disorder and bipolar disorder.

Each possibility represents a separate embodiment of the present invention.

According to other embodiments, the depression is associated with other psychiatric disorders selected from the group consisting of dysthymia, posttraumatic stress disorder, post-partum depression, schizophrenia, schizoaffective disorder, anxiety disorder (including obsessive compulsive disorder, generalized anxiety disorder, panic disorder and social phobia), eating disorders including anorexia nervosa and bulimia, Parkinson's disease, Alzheimer's disease, fibromyalgia and chronic fatigue syndrome. Each possibility represents a separate embodiment of the present invention.

According to yet additional embodiments, the depression is associated with a general medical condition selected from the group consisting of heart disease, cancer, diabetes, HIV/AIDS and neurological conditions (including stroke and multiple sclerosis). Each possibility represents a separate embodiment of the present invention.

According to further embodiments, the depression is associated with alcohol and/or drug abuse.

According to additional aspect, the present invention provides a method for treating a subject affected with or susceptible to be affected with at least one of obsessive compulsive disorder, panic disorder, generalized anxiety disorder, pre-menstrual syndrome (PMS), posttraumatic stress disorder, social phobia, agoraphobia, fibromyalgia, chronic fatigue syndrome chronic pain, bulimia, anorexia nervosa, obesity, alcohol abuse, smoking cessation and nicotine withdrawal syndrome symptoms the method comprises administering to the subject a therapeutically effective amount of a compound that inhibits the activity of Type III deiodinase (DIO3) or a pharmaceutical composition comprising same. Each possibility represents a separate embodiment of the present invention.

According to certain exemplary embodiments, the compound that inhibits the activity of Type III deiodinase (DIO3) is a compound of the present invention as described herein.

According to yet additional aspect, the present invention provides a method for treating or preventing cancer, the method comprises administering to a subject in need thereof a therapeutically effective amount of the compound of the invention that inhibits the activity of Type III deiodinase (DIO3) or a pharmaceutical composition comprising same, thereby treating or preventing cancer.

According to certain embodiments, the cancer is selected from the group consisting of ovarian cancer, endometrial cancer, neuroblastoma, colon cancer, hepatic cancer, basal cell carcinoma and breast cancer. Each possibility represents a separate embodiment of the present invention.

According to certain exemplary embodiments, the cancer is ovarian cancer.

According to certain embodiments, inhibition of DIO3 activity results in increased amount of T3 in the subject. According to currently certain exemplary embodiments, the amount of T3 is increased in the brain of the subject.

According to certain embodiments, the treatment results in a diminishment or elimination of depression and/or its symptoms.

Compounds useful in treating and/or preventing any of the diseases or conditions described herein are compounds of formula (I), for example compounds of formulae (II) or (III) as exemplified herein. Additional compounds useful in treating and/or preventing any of the diseases or conditions described herein are compounds of formula (I-A):

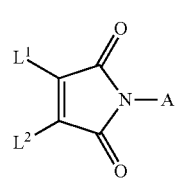

(I-A)

wherein
A is

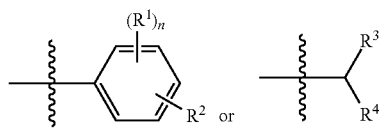

$R^1$ is independently at each occurrence a halogen, OH, $NO_2$ or $N(R)2$ wherein each R is independently H or a $C_1$-$C_6$ alkyl;
$R^2$ is COOH, OH, $NO_2$, $N(R)_2$ or a linear or branched $C_1$-$C_6$ alkyl substituted with at least one group selected from the group consisting of COOH, halogen, OH, $NO_2$, and $N(R)2$;
$R^3$ is H or COOH;
$R^4$ is iodophenyl, heterocyclyl, heteroaryl, the side chain of an amino acid selected from the group consisting of a naturally occurring alpha-amino acid, 3,4-dihydroxyphenylalanine (DOPA) and iodotyrosine; or $R^4$ is represented by the structure:

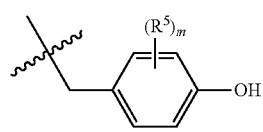

wherein $R^5$ is independently at each occurrence OH, halogen, $NO_2$ or $N(R)_2$ and m is 0, 1, 2, 3 or 4;
$L^1$ and $L^2$ are each a leaving group selected from a halogen and a sulfonate;
n is 0, 1, 2, 3 or 4;
and salts thereof.

Currently preferred compounds according to the present invention are represented by the structure of formula 3, 4, 5, 6, 7, 8, 9, 10, 11 or 12, with each possibility representing a separate embodiment of the present invention.

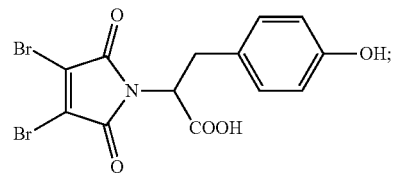

3

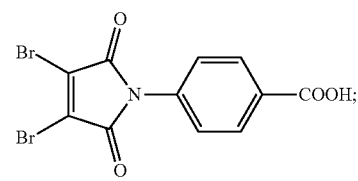

4

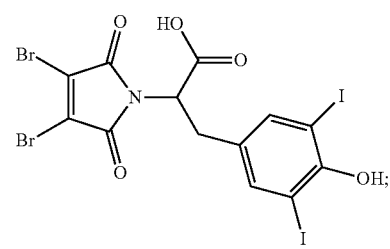

5

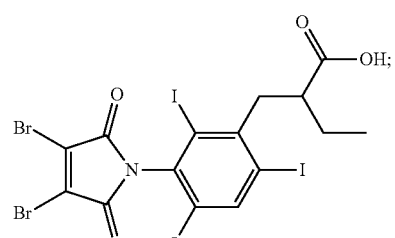

6

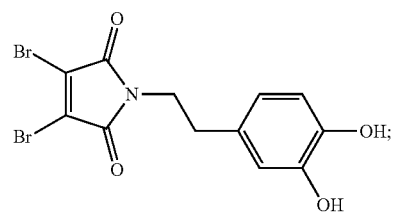

7

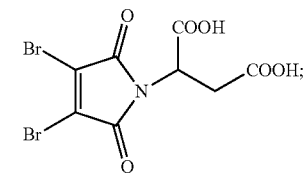

8

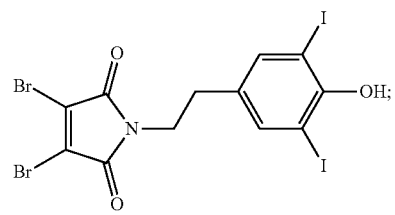

9

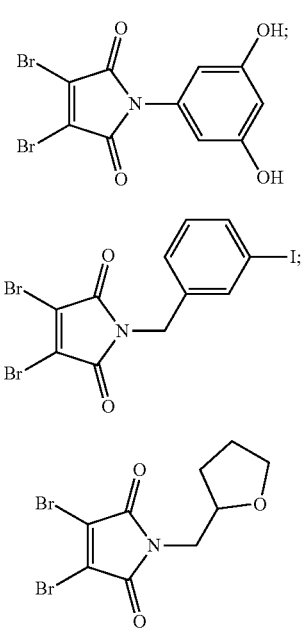

and salts thereof.

Each of said compounds can be used alone or in a pharmaceutical composition in the context of the present invention.

According to certain typical embodiments, the compound specifically inhibits the activity of DIO3. Typically, the compound is identified according to the teachings of the present invention and has the general formula I or II or III or I-A, or any of the compounds encompassed for such formulae as disclosed herein. However, it is to be explicitly understood that other compounds having specificity to DIO3 inhibition are encompassed within the scope of the present invention.

According to other typical embodiments, the subject is human.

Other objects, features and advantages of the present invention will become clear from the following description and drawings.

DETAILED DESCRIPTION OF THE INVENTION

Figure 1:
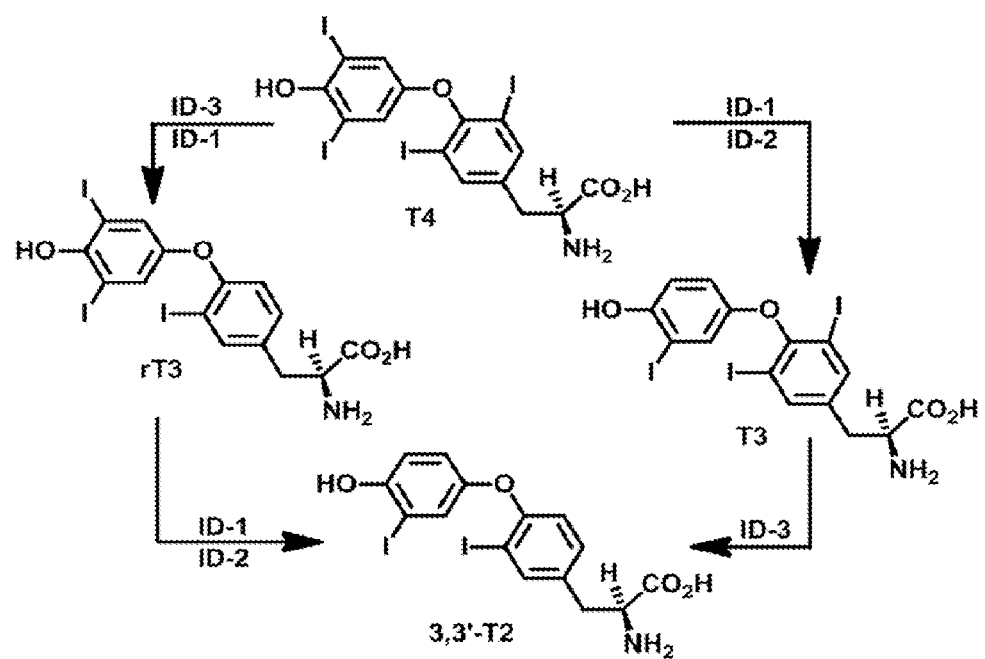
FIG. 1 demonstrate activation and inactivation of thyroid hormones by the three iodothyronine deiodinases DIO1 (ID-1), DIO2 (ID-2) and DIO3 (ID-3).

The present invention provides novel compounds that specifically inhibit the activity of Type III deiodinase (DIO3). DIO3 is particularly active in the brain, and DIO3 inhibition may thus result in an increased amount of the hormone 3,3',5,-triiodothyronine (T3) in brain. DIO3 has also been indicated to be associated with hyperproliferative states and with human solid tumors. Specifically, previous studies reported elevated expression and activity of DIO3 in a number of human cancer diseases (Dentice et al. 2013, ibid).

The present invention discloses for the first time that inhibition of DIO3 activity is useful for treating and/or preventing depression. Without wishing to be bound by certain specific theory or mechanism of action, inhibition of DIO3 by the compounds of the invention leads to elevated content of T3 in the brain. The novel compounds of the present invention are also useful for treating and/or preventing cancer and other diseases or disorders associated with elevated expression or activity of DIO3.

Definitions

The term "$C_1$-$C_6$ alkyl" as used herein alone or as part of another group refers to any saturated aliphatic hydrocarbon, including straight-chain, and branched-chain which contains 1 to 6 carbon atoms. Examples of C1-C6 alkyl groups include methyl, ethyl, n-propyl, isopropyl, n-butyl, sec-butyl, isobutyl, t-butyl, 1-penyl, 2-pentyl, 3-pentyl, 1-hexyl, 2-hexyl, and 3-hexyl. According to the principles of the present invention, the C1-C6 alkyl group is substituted at any location with a COOH moiety.

The term "tyrosine side chain" refers to the following moiety:

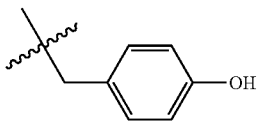 [SMILES: *Cc1ccc(O)cc1]

The term "iodotyrosine side chain" refers to a tyrosine side chain in which one or more of the phenyl hydrogens have been substituted by iodine. One non-limiting example of an iodotyrosine side chain is a 3-5-diiosotyrosine group represented by the moiety:

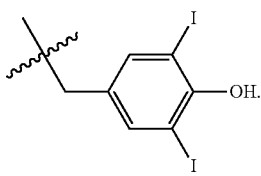 [SMILES: *Cc1cc(I)c(O)c(I)c1]

The term "hydroxytyrosine side chain" refers to a tyrosine side chain in which one or more of the phenyl hydrogens have been substituted by a hydroxy. One non-limiting example of a hydroxytyrosine side chain is 3-hydroxytyrosine group (alternatively designated 3,4-dihydroxyphenylalanine), which is represented by the moiety:

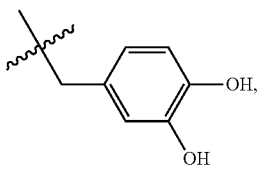 [SMILES: *Cc1ccc(O)c(O)c1]

also known as "DOPA".

The term "aspartic acid side chain" refers to the group —CH$_2$—COOH.

The term "ethyl diiodophenol" refers to an ethylphenol group in which two of the phenol hydrogens have been substituted by iodine. One non-limiting example of an ethyl diiodophenol is represented by the moiety:

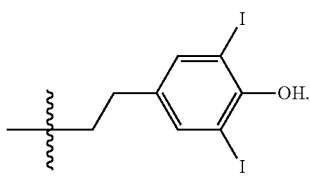 [SMILES: *CCc1cc(I)c(O)c(I)c1]

Several of the compounds of the present invention contain side chains of naturally occurring alpha-amino acids. The naturally occurring amino acids are, e.g., glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Each possibility represents a separate embodiment of the present invention.

The term "depression" as used herein includes, but is not limited to, major depressive episodes in the context of major depressive disorder or bipolar disorder, schizoaffective disorder and other psychiatric states that are characterized by depressed mood and/or feelings of sadness, despair, discouragement, "blues", melancholy, feelings of low self esteem, guilt and self reproach, withdrawal from interpersonal contact, and somatic symptoms such as eating and sleep disturbances.

It is to be explicitly understood that the present invention encompasses treating depression that is associated with other psychiatric disorders, with general medical conditions or with alcohol or drug abuse.

Examples of other psychiatric disorders that may be associated with depression include, but are not limited to, dysthymia, posttraumatic stress disorder, schizophrenia, schizoaffective disorder, post-partum depression, eating disorders including anorexia nervosa and bulimia, anxiety disorders, Parkinson's disease, Alzheimer's disease, fibromyalgia and chronic fatigue syndrome.

Anxiety disorders include, but are not limited to, obsessive compulsive disorder, generalized anxiety disorder, panic disorder and social phobia.

Examples of general medical conditions associated with depression include, but are not limited to, heart diseases, cancer, diabetes, HIV/AIDS and neurological conditions such as stroke and multiple sclerosis.

The present invention also encompasses treating disease and conditions known to be amenable to treatment with anti-depressants other than the compounds of the present invention. According to certain embodiments, such diseases or conditions include, but are not limited to, obsessive compulsive disorder, panic disorder, generalized anxiety disorder, pre-menstrual syndrome (PMS), posttraumatic stress disorder, social phobia, agoraphobia, fibromyalgia, chronic fatigue syndrome chronic pain, bulimia, anorexia nervosa, obesity, alcohol abuse, smoking cessation and nicotine withdrawal syndrome symptoms.

The term "cancer" refers to a medical condition characterized by abnormal cell growth in a tissue. The term encompasses a wide range of cancers, classified according to cell type origin, including, without limitation, carcinomas, sarcomas, myelomas, leukemias and lymphomas. Particular types of cancers, classified according to the affected tissue, include, without limitation, brain cancer, lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, and kidney cancer. Further cancer types, include, without limitation, hepatocellular carcinoma, hematoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to some embodiments, the cancer is associated with aberrant DIO3 expression. A cancer associated with aberrant expression of DIO3 is one in which DIO3 expression or activity results in a level of active DIO3 that is greater than that observed in corresponding (similar cell types) non-cancerous cells. In other embodiments, it is a cancer associated with low levels of active T3. A cancer associated with low levels of T3 is one in which functional or active T3 is lower than in a corresponding non cancerous cell.

According to certain embodiments, the compounds of the invention are for treating solid tumors.

As used herein, the terms "type III deiodinase", "type III iodothyronine deiodinase", type 3 deiodinase", "type 3 iodothyronine deiodinase", DIO3 and D3 are used herein interchangeably and refer to a protein belonging to the iodothyronine deiodinase family that catalyzes the inactivation of thyroid hormone by inner ring deiodination of the prohormone thyroxine (T4) and the bioactive hormone 3,3',5-triiodothyronine (T3) to inactive metabolites, 3,3',5'-triiodothyronine (rT3) and 3,3'-diiodothyronine (3,3'-T2), respectively.

As used herein, the term "inhibition" with regard to inhibiting the activity of DIO3 refers to reducing the activity of DIO3 compared to its activity under the same conditions without the addition of an inhibitory compound. According to certain embodiments, the DIO3 activity is reduced by at least 5%, 10%, 20%, 30%, 40%, 50%, 60%, 70%, 80%, 90%, 95%, 99% or 100% compared to its activity under the same conditions without the addition of an inhibitory compound. Each possibility represents a separate embodiment of the present invention.

The term "specific inhibition" with regard to the inhibition of DIO3 by the compounds of the present invention refers to compounds which inhibit DIO3 to a greater extent (e.g., a lower $K_i$) than it inhibits DIO2 or DIO1 enzymes. A specific DIO3 inhibitor also includes agents that inhibit DIO3, but fail to inhibit DIO2 or DIO1 at comparable concentrations.

The term "therapeutically effective amount" refers to the amount of a compound of the present invention that, when administered to a subject in need thereof, results in inhibition of DIO3 activity. According to certain embodiments, inhibition of DIO3 activity results in increased T3 amounts in the brain compared to the amounts observed in other organs.

The term "preventing" as used herein means causing the clinical symptoms of the disease state not to develop in a subject that may be exposed to or predisposed to the disease state, but does not yet experience or display symptoms of the disease state.

The term "treating: as used herein refers to inhibiting the disease state, i.e., arresting the development of the disease state or its clinical symptoms, or relieving the disease state, i.e., causing temporary or permanent regression of the disease state or its clinical symptoms. The term is interchangeable with any one or more of the following: abrogating, ameliorating, inhibiting, attenuating, blocking, suppressing, reducing, halting, alleviating or preventing symptoms associated with the disease.

According to one aspect, the present invention provides a compound having the general formula I:

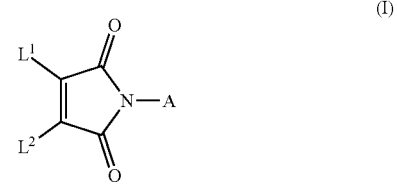

wherein
A is

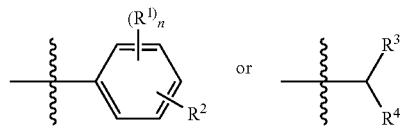

$R^1$ is independently at each occurrence a halogen, OH, $NO_2$ or $N(R)_2$ wherein each R is independently H or a $C_1$-$C_6$ alkyl;

$R^2$ is COOH, OH, $NO_2$, $N(R)_2$ or a linear or branched $C_1$-$C_6$ alkyl substituted with at least one group selected from the group consisting of COOH, halogen, OH, $NO_2$, and $N(R)2$;

$R^3$ is H or COOH;

$R^4$ is iodophenyl, heterocyclyl, heteroaryl, or the side chain of an amino acid selected from the group consisting of tyrosine, 3,4-dihydroxyphenylalanine (DOPA), iodotyrosine, aspartic acid, valine, leucine, isoleucine, methionine, tryptophan, threonine, asparagine, glutamine, cysteine, proline, arginine, histidine, lysine, glutamic acid; or $R^4$ is represented by the structure:

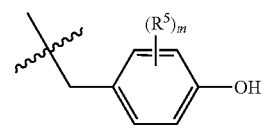

wherein $R^5$ is independently at each occurrence OH, halogen, $NO_2$ or $N(R)_2$ and m is 0, 1, 2, 3 or 4;

$L^1$ and $L^2$ are each a leaving group selected from a halogen and a sulfonate;

n is 1, 2, 3 or 4;

and salts thereof.

In one embodiment, the compound of formula (I) is a phenylcarboxylic acid derivative (e.g., p-benzoic acid derivative or iopanoic acid derivative), represented by the structure of formula (II):

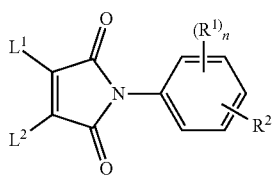
(II)

In another embodiment, the compound of formula (I) is represented by the structure of formula (III):

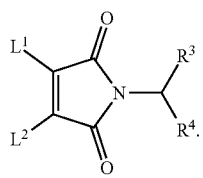
(III)

Compounds useful in treating and/or preventing any of the diseases or conditions described herein are compounds of formula (I), for example compounds of formulae (II) or (III). Additional compounds useful in treating and/or preventing any of the diseases or conditions described herein are compounds of formula (I-A):

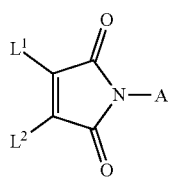
(I-A)

wherein
A is

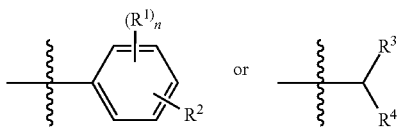

$R^1$ is independently at each occurrence a halogen, OH, $NO_2$ or $N(R)_2$ wherein each R is independently H or a $C_1$-$C_6$ alkyl;

$R^2$ is COOH, OH, $NO_2$, $N(R)_2$ or a linear or branched $C_1$-$C_6$ alkyl substituted with at least one group selected from the group consisting of COOH, halogen, OH, $NO_2$, and $N(R)_2$;

$R^3$ is H or COOH;

$R^4$ is iodophenyl, heterocyclyl, heteroaryl, the side chain of an amino acid selected from the group consisting of a naturally occurring alpha-amino acid, 3,4-dihydroxyphenylalanine (DOPA) and iodotyrosine; or $R^4$ is represented by the structure:

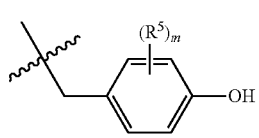

wherein $R^5$ is independently at each occurrence OH, halogen, $NO_2$ or $N(R)_2$ and m is 0, 1, 2, 3 or 4;
$L^1$ and $L^2$ are each a leaving group selected from a halogen and a sulfonate;
n is 0, 1, 2, 3 or 4;
and salts thereof.

Preferred embodiments of formula I, I-A and II are compounds of formula 3, 4, 5, 6, 7, 8, 9, 10, 11 or 12, as described herein, and salt thereof.

One or more of the compounds of the invention, may be present as a salt. The term "salt" encompasses salts formed by standard acid-base reactions between an acidic moiety and an organic or inorganic cation. The term "organic or inorganic cation" refers to counter-ions for the carboxylate anion of a carboxylate salt or the counter ion for the phenoxide moiety. The counter-ions are chosen from the alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl) ammonium, phenylethylbenzylammonium, dibenzylethylenediammonium, and like cations.

The present invention also includes solvates of any of compounds described herein. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

According to another aspect, the present invention provides a pharmaceutical composition comprising at least one compound of the present invention and a pharmaceutically acceptable diluents or carrier.

As sued herein, the term "pharmaceutically acceptable carrier or excipient" means an additive, carrier, excipient or diluent which is useful in preparing a pharmaceutical composition that is generally safe non-toxic, and neither abrogates nor causes otherwise undesirable effect to the administered compound. The term includes such additives that are acceptable for human as well as veterinary pharmaceutical use.

The term "subject" includes humans and animals amenable to therapy with a DIO3 inhibitor including animals afflicted with cancer or depression or depression associated disease or disorder. According to some embodiments, the subject is a human subject. Each possibility represents a separate embodiment of the invention.

The term "subject" as used herein, includes, for example, a subject who has been diagnosed to be afflicted with cancer or depression or depression associated disease or disorder or a subject who has been treated to ameliorate cancer or depression or depression associated disease or disorder, including subjects that have been refractory to the previous treatment. Also encompassed within the present invention is a healthy subject having a risk of being affected with cancer or depression or depression associated disease or disorder.

According to some embodiments, the subject is afflicted with cancer and has been identified to express DIO3 by the tumor. According to some embodiments, the expression is overexpression and the overexpression is determined following analysis and comparison with control or reference. According to some embodiments, the control is selected from the group consisting of: a predetermined cutoff value, a value obtained from a healthy individual, a panel of values from a set of healthy individuals and a value or a set of values obtained from a group of individuals afflicted with defined severities of cancer. Each possibility represents a separate embodiment of the invention. According to yet another embodiment, the predetermined cutoff value is obtained from the subject to be treated at at-least one prior-referenced time point.

According to some embodiments, the expression of DIO3 may be determined by any method known in the art, for example by an immunoassay.

The pharmaceutical compositions of the invention can be prepared by methods and contain carriers which are well-known in the art, for example as described in Remington: The Science and Practice of Pharmacy, Alfonso R. Gennaro, editor, 20th ed. Lippincott Williams & Wilkins: Philadelphia, Pa., 2000.

In general, the compounds of the invention are administered in a therapeutically effective amount by any of the accepted modes of administration for agents that serve similar utilities. Suitable dosage ranges are depending upon numerous factors such as the severity of the symptoms to be treated, the age and relative health of the subject, the potency of the compound used; the route and form of administration; and the specific indication towards which the administration is directed. One of ordinary skill in the art of treating such conditions will be able, without undue experimentation and in reliance upon personal knowledge and the disclosure of this Application, to ascertain a therapeutically effective amount of the compounds of the present invention for a given condition.

Compounds of the invention may be administered as pharmaceutical formulations including those suitable for parenteral administration (including intramuscular, subcutaneous and intravenous), oral administration (including buccal and sub-lingual), nasal, topical, pulmonary, intrathecal administration, or administration by inhalation. A preferred manner of administration is generally oral using a convenient daily dosage regimen which can be adjusted according to the degree of affliction. According to one embodiment, the DIO3 inhibitor is administered locally into the tissue to be treated. According to one embodiment, the tissue is a brain tissue, and the administration route is directly into the brain tissue.

According to some embodiments, the composition comprising a DIO3 inhibitor may further comprise an additional agent. The additional agent may be any treatment for cancer, depression or depression associated disease or condition. According to some embodiments, treatment comprises administering to a subject in need thereof a plurality of DIO3 inhibitors.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of sterile injectable solutions for parenteral use.

According to yet additional aspect, the present invention provides a method for treating or preventing depression or a depression-associated disease or condition, the method comprises administering to a subject in need thereof a therapeutically effective amount of a compound that inhibit the activity of Type III deiodinase (DIO3) thereby treating or preventing depression a depression-associated disease or condition.

According to certain embodiments, inhibition of the DIO3 activity results in increased amount of T3 in the subject. According to currently certain exemplary embodiments, the amount of T3 is increased in the brain of the subject.

In some embodiments, the compounds of the present invention are designed to have specificity or some selectivity to inhibition of DIO3, such that the other deiodinases (DIO1 and DIO2) are not inhibited or inhibited to a lesser extent. DIO3 is known to be found primarily in the brain, and, more importantly, it is not found in heart or bone tissue. Thus, the specific inhibition of DIO3 results in increased amount of T3 in the brain, where it is most required to assert its anti-depressant activity, while having none or negligible of the deleterious side effects associated with non-specific elevation of T3 concentration, including enhancement of bone depletion, muscle weakness and tachycardia (Ocasio and Scanlan, *Current Opinion in Endocrinology and Diabetes* 2005; 12, 363-370; Yoshihara and Scanlan, *Curr Top Med Chem* 2003; 3, 1601-1616).

In some embodiments, the compounds of the invention also inhibit DIO1 and DIO2, in addition to DIO3, but they are designed to selectively target the brain, or they are formulated specifically for brain delivery, such that they target DIO3 selectively due to preferential localization to the brain.

According to yet another aspect, the present invention provides a method for treating or preventing cancer, the method comprises administering to a subject in need thereof a therapeutically effective amount of a compound of the present invention.

DIO3 expression and activity have been indicated previously to be associated with tumorigenesis. Thus, according to further embodiments the compounds of the present invention, which inhibit DIO3 are useful as treatment for cancer.

According to some embodiments, the cancer is a solid cancer. Non limiting examples of solid cancers which are encompassed within the embodiments of the present invention include pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; melanoma; neuroendocrine cancer; brain tumors.

According to some embodiment, the cancer is colon cancer or basal cell carcinoma (BCC).

According to certain exemplary embodiments, the cancer is ovarian cancer, endometrial cancer.

According to some embodiments, the compounds of the invention are designed to selectively target overproliferating cells, particularly cancer cells, or they are formulated specifically for delivery into these types of cells such that they target DIO3 selectively due to preferential localization within these cells.

The DIO3 inhibitors of the present invention may be administered by any suitable route of administration. According to some embodiments, the DIO3 inhibitor is prescribed for a chronic administration. Chronic administration may be performed, for example, by a single dose, once daily. According to some embodiments, the DIO3 inhibitor is prescribed for acute administration.

The therapeutically effective amount of a compound of the invention to be administered to a subject depends on the condition to be treated and subject parameters including, but not limited to, gender, age, weight type and severity of the condition. The therapeutically effective amount can be initially assessed from in vitro assays. Target concentrations will be those concentrations of active compound(s) that are capable of inhibiting DIO3 activity by at least about 5%-95% in comparison to DIO3 activity in untreated cell, either normal or overproliferating cells. Target concentrations of active compound(s) that are capable of inhibiting DIO3 by at least about 60-70% or even 90% or higher in in vitro assays are preferred.

Therapeutically effective amounts for use in humans can also be determined from animal models. For example, a dose for humans can be formulated to achieve a circulating concentration that has been found to be effective in animals. Animal models of cancer and for depression assessment are known in the art. For treating cancer, the dosage in humans can be adjusted by monitoring inhibition of cell proliferation and/or tumor growth and adjusting the dosage upwards or downwards, to achieve the desired percentage of inhibition. For treating depression, the dosage in humans can be adjusted in view of the effective dosage that alleviated or abolishes the depression associated symptoms. Adjusting the dose to achieve maximal efficacy in humans based on the methods described above and other methods as are well-known in the art is well within the capabilities of the ordinarily skilled artisan.

It is to be explicitly understood that any mechanism by which inhibition of DIO3 activity overcomes depression or depression associated disease or disorder is encompassed within the scope of the present invention. It has been previously acknowledged that the phenomena attributed to T3 may be mediated by T3 activation of gene transcription. Accordingly, most of the reports regarding the use of T3 as antidepressant describe positive influence of T3 administration after a lag time of about a week. However, other antidepressants are known to have immediate effect. For example, ketamine has been reported to have anti-depression activity after acute administration to humans (Aan Het Rot et al. Biological Psychiatry, 2012; 72(7), 537-547), and to affect the behavioral performance of rats in forced swim test (FST) (Yang C. et al., 2012. Journal of Biomedicine and Biotechnology, Epub 2012 Apr. 8).

It has been also described that in addition to being active by induction of gene transcription the thyroid gland hormones show immediate physiological effects. Thus, without wishing to be bound by any specific theory or mechanism of action, administration of DIO3 inhibitors can assert immediate antidepressant effects.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Design and Synthesis of DIO3 Mimics

To date, pure DIO3 enzyme is not available. An inventor of the present invention and co-workers have designed and synthesized molecules that functionally mimic DIO3 in terms of deiodinase activity (Manna et al., 2010, ibid; Manna et al., 2012, ibid). Such DIO3-mimetic molecules have now been utilized for design and synthesis of compounds capable of inhibiting DIO3 enzyme. The present invention discloses such compounds that functionally inhibit the activity of the DI03-mimetic molecule and the wild-type (wt) DIO3 enzyme.

Figure 2:
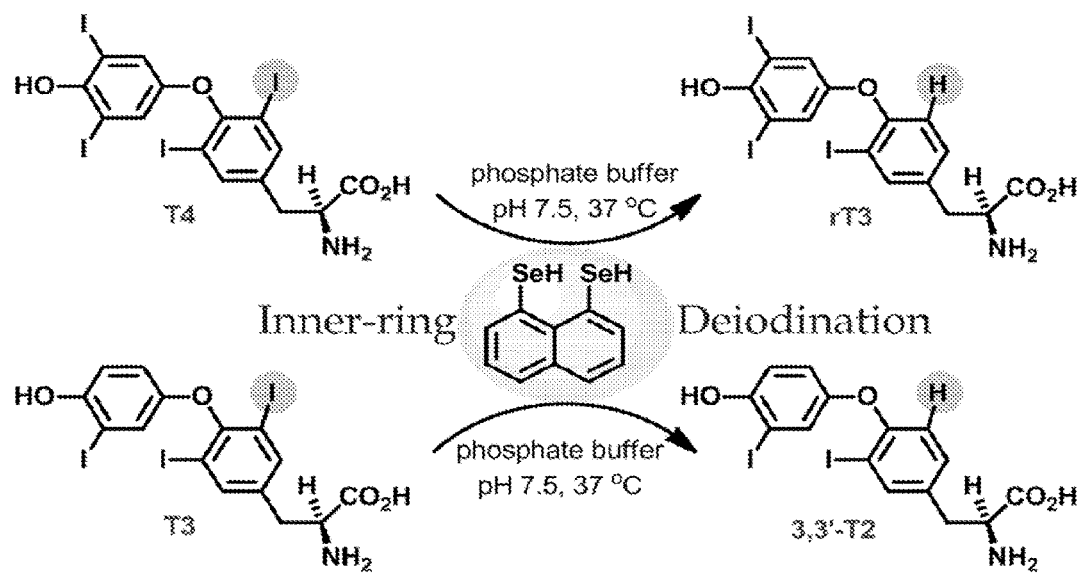
FIG. 2 shows inner ring monodeiodination of T4 to rT3 or of T3 to 3,3'-T2 by DIO3 mimic (compound A).
Figure 3:
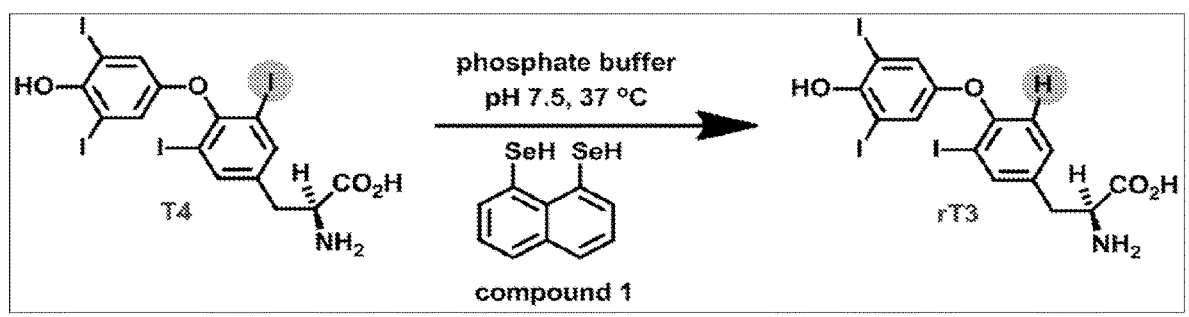
FIG. 3 demonstrates deiodination of thyroxine by compound A, a DIO3 mimic.

The deiodination of thyroxine by compound A (a DIO3 mimetic; FIGS. 2 and 3) in the presence of various thiourea derivatives was studied. When the commonly used antithyroid drugs such as thiourea derivatives (e.g., 6-n-propyl-2-thiouracil (PTU), 6-methyl-2-thiouracil (MTU) and 1-methyl-3H-imidazole-2-thione or methimazole (MMI)) were used, no inhibition of the deiodinase activity was observed. Although PTU and MTU have been shown to inhibit DIO1, these compounds do not inhibit DIO3. Specifically, thiourea compounds (e.g., PTU) have been shown to react with the selenenyl iodide intermediate of DIO1. Those results suggest that compound A not only deiodinates T4 in the inner-ring, but also behaves similarly to DIO3 with respect to inhibition. These studies suggest that thiourea-based compounds are not suitable as inhibitors for DIO3.

Another known inhibitor of DIO1, i.e. iodoacetic acid (IAA), may react with the selenol group of the enzyme. This compound is specific for DIO1 and cannot inhibit DIO2 and DIO3. Although IAA can effectively inhibit the activity of several Cys peptidases (i.e., the Sec-containing glutathione peroxidase (GPx), and thioredoxin reductase (TrxR)) by forming the corresponding alkylated Cys or Sec derivatives, the reason for the insensitivity of DIO3 toward IAA is not clear. Treatment of compound A with IAA resulted in a deiodination instead of the formation of Se-carboxymethylated derivative. In contrast, a compound that lacks the second selenol moiety underwent facile carboxymethylation by IAA. These observations suggest that IAA may undergo rapid deiodination in the presence of DIO3, which may account for the insensitivity of this enzyme toward IAA.

A careful analysis of the amino acid residues at the active site of DIO3 indicates that there is a cysteine (Cys) residue in the enzyme that may assist the selenocysteine (Sec) in the deiodination reaction. In the mimic, the second selenol moiety in the 8-position of the naphthalene ring is expected to perform a similar function. The current approach aims at targeting both the Sec and Cys instead of targeting the Sec alone. Previous attempts to develop inhibitors for DIO3 based on Sec reactivity were unsuccessful.

As described above, it is contemplated that any compound that can react with the both selenol moieties simultaneously in the synthetic DIO3 mimic of compound A may inhibit the deiodinase activity of this compound.

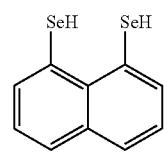

(A)

Without wishing to be bound by any particular mechanism or theory, it was hypothesized that the dibromomaleimide derivatives of the present invention may inhibit the activity of the DIO3 mimic by reacting with the two selenol groups to form a stable adduct.

In view of the above, the following compounds (compound B and C) were synthesized. The two simultaneous nucleophilic attacks of the selenol moieties at the carbons adjacent to the carbonyl groups are expected to block the selenium centers. The reactions of compound A with compounds B (2,3-dibromo-N-benzylmaleimide) and C (2,3-dibromo-N-methylmaleimide) were studied. The reaction of compound A with compounds B and C produced the adducts D (1,8-bis(2,3-diseleno-N-benzylmaleimide)naphthalene) and E (1,8-bis(2,3-diseleno-N-methylmaleimide)naphthalene).

B
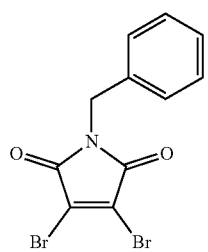

C
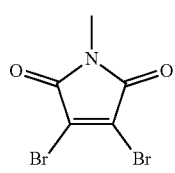

D
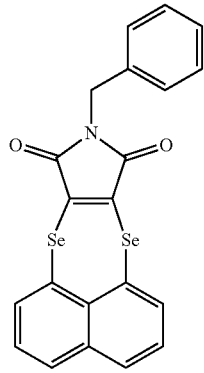

E
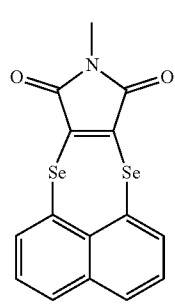

Figure 4:
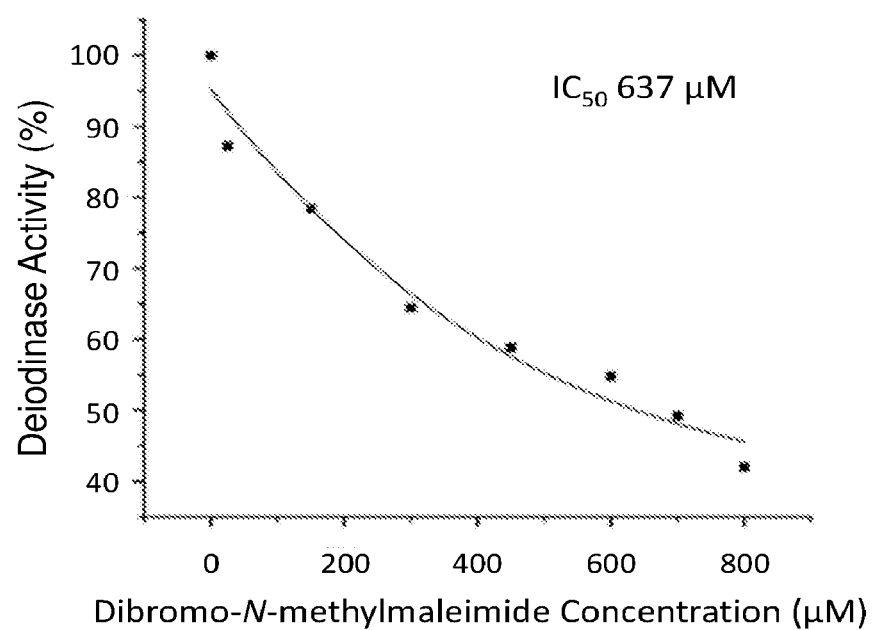
FIG. 4 shows Inhibition of DIO3 mimic by Compound C (Dibromo-N-methylmaleimide).

Subsequently, the deiodination of T4 by compound A in the presence of compounds B and C was studied. The results demonstrate that compounds B and C do inhibit the deiodination of T4 (exemplified in FIG. 4 for compound C).

Another compound, a novel tyrosine derivative 3 (TYR-DBRMD) was synthesized. The following description demonstrates the route employed for the synthesis of TYR-DBRMD.

Synthesis of TYR-DBRMD (Compound 3)

The novel tyrosine derivative 3 was obtained from dibromomaleic anhydride (1) and L-tyrosine. As the commercially available starting material (compound 2) is expensive, it was prepared from maleic anhydride (1) in a sealed Teflon tube by using aluminum chloride as catalyst. For the synthesis of compound 2, the procedure reported in Dubernet et al. (Dubernet, M. et al., Tetrahedron, 2005; 61, 4585-4593) was followed:

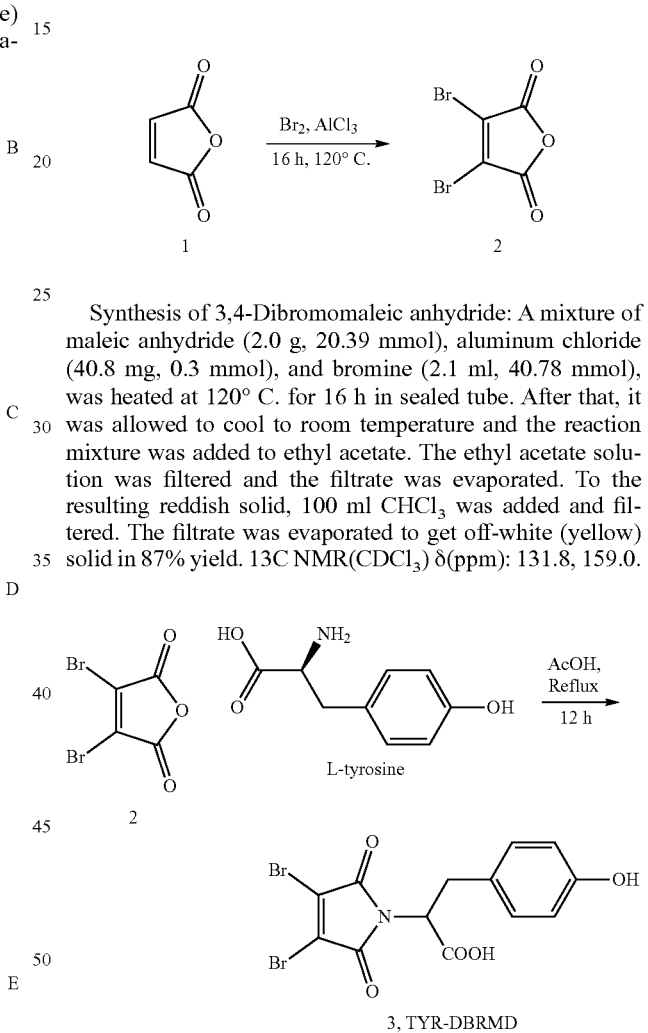

Synthesis of 3,4-Dibromomaleic anhydride: A mixture of maleic anhydride (2.0 g, 20.39 mmol), aluminum chloride (40.8 mg, 0.3 mmol), and bromine (2.1 ml, 40.78 mmol), was heated at 120° C. for 16 h in sealed tube. After that, it was allowed to cool to room temperature and the reaction mixture was added to ethyl acetate. The ethyl acetate solution was filtered and the filtrate was evaporated. To the resulting reddish solid, 100 ml $CHCl_3$ was added and filtered. The filtrate was evaporated to get off-white (yellow) solid in 87% yield. 13C NMR($CDCl_3$) δ(ppm): 131.8, 159.0.

To a solution of 3,4-dibromomaleic anhydride (500 mg, 1.95 mmol) in acetic acid (10 ml), tyrosine (425 mg, 2.35 mmol) was added. The mixture was heated at reflux condition for 12 h. The solvent was removed under reduced pressure. The crude mixture was purified by column chromatography over silica gel using petroleum ether and ethyl acetate as mobile phase to afford the desired product (485 mg, 59%) as off-white solid.

Figure 6:
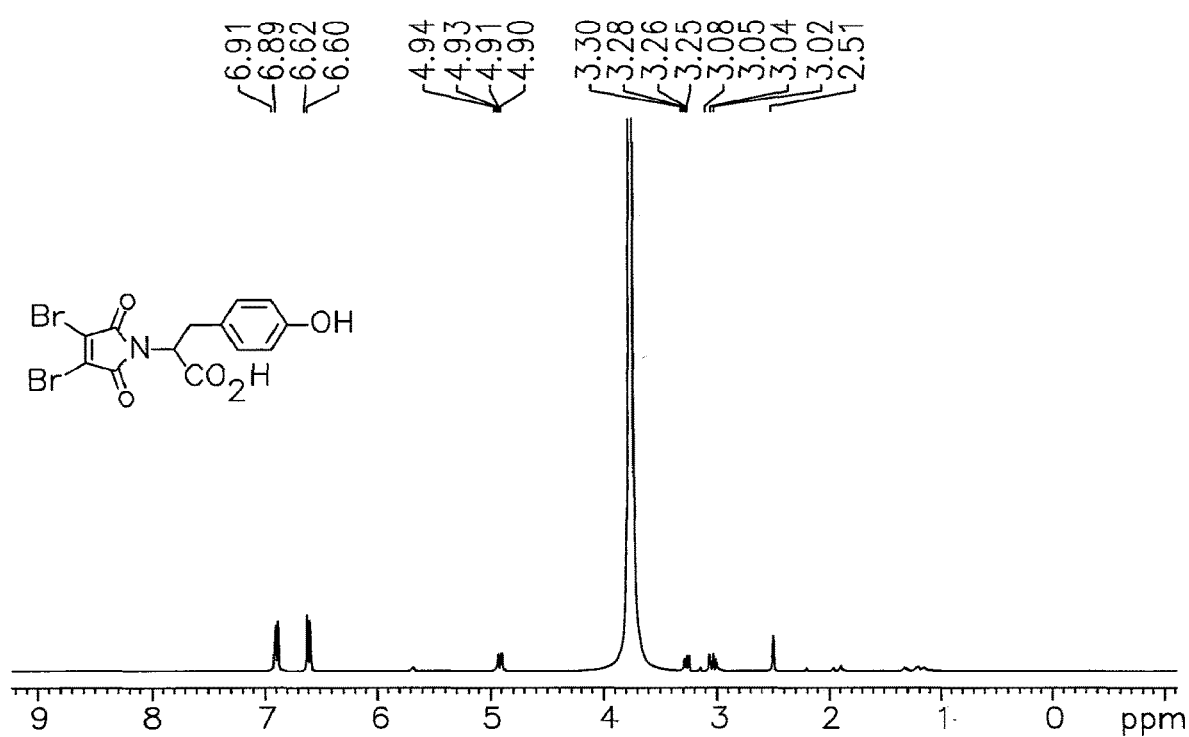
FIG. 6 shows $^1$H NMR spectra of compound 3 in DMSO-$d_6$.

$^1$H NMR(DMSO-$d_6$) δ (ppm): 3.02-3.08 (1H, m), 3.25-3.30 (1H, m), 4.90-4.94 (1H, dd, J=8.0 Hz) 6.60 (2H, d, J=8.0 Hz), 6.89 (2H, d, J=8.0 Hz) (FIG. 6).

Figure 7:
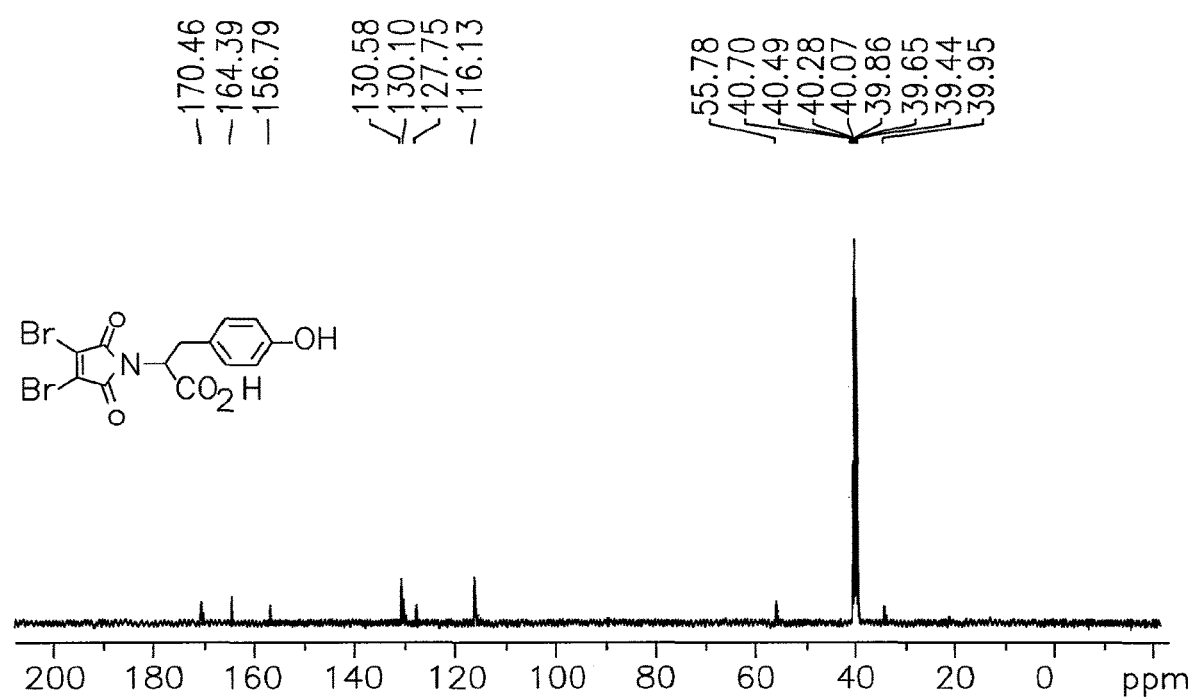
FIG. 7 shows $^{13}$C NMR spectra of compound 3 in DMSO-$d_6$.

$^{13}$C NMR($CDCl_3$) δ (ppm): 33.9, 55.8, 116.1, 127.7, 130.1, 130.6, 156.8, 168.4, 170.5 (FIG. 7).

m.p. 175-177° C.

Synthesis of PBENZ-DBRMD (Compound 4):

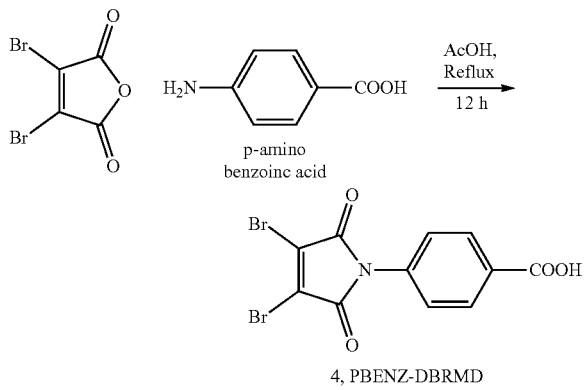

4, PBENZ-DBRMD

To a solution of 3,4-dibromomaleic anhydride (500 mg, 1.95 mmol) in acetic acid (10 ml), p-amino benzoic acid (322 mg, 2.35 mmol) was added. The mixture was heated at reflux condition for 12 h. The solvent was removed under reduced pressure. The crude mixture was purified by column chromatography over silica gel using petroleum ether and ethyl acetate as mobile phase to afford the desired product (550 mg, 82%) as yellow solid.

Figure 8:
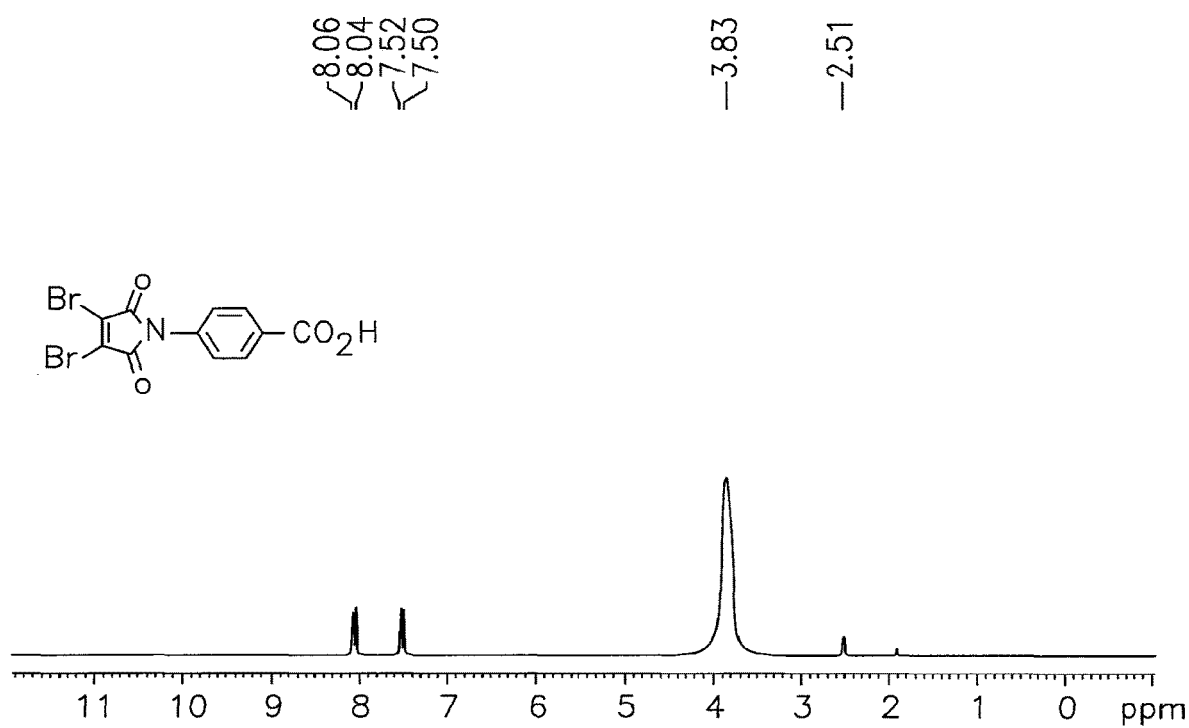
FIG. 8 shows $^1$H NMR spectra of compound 4 in DMSO-$d_6$.

$^1$H NMR(DMSO-d$_6$) δ (ppm): 7.50 (2H, d, J=8.0 Hz), 8.04 (2H, d, J=8.0 Hz) (FIG. 8).

Figure 9:
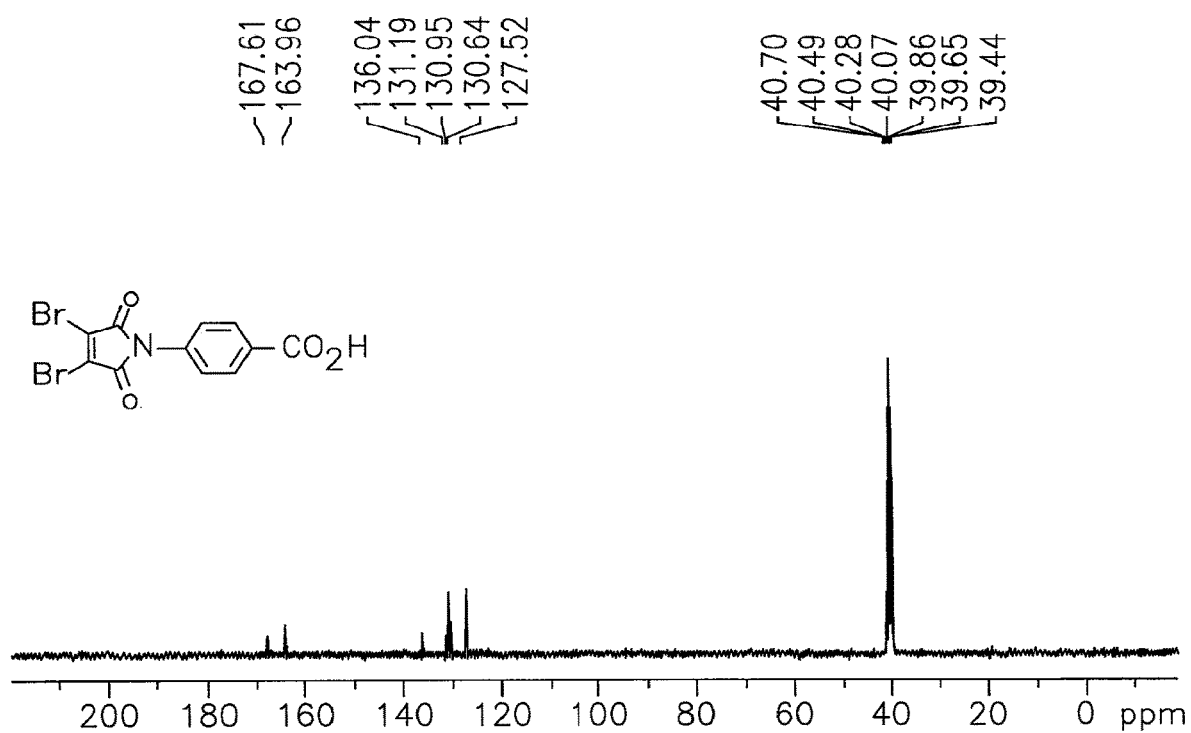
FIG. 9 shows $^{13}$C NMR spectra of compound 4 in DMSO-$d_6$.

$^{13}$C NMR(DMSO-d$_6$) δ (ppm):127.5, 130.6, 130.9, 131.1, 136.0, 163.9, 167.6 (FIG. 9).

Example 2: Deiodination Assay

The deiodination reactions were carried out in 100 mM phosphate buffer (pH 7.5) with 10 mM dithiothreitol (DTT) at 37° C. Diselenol (Compound A) was freshly prepared by reducing the corresponding diselenide, with NaBH4 prior to use. The reaction products were analyzed by reverse-phase HPLC (Lichrospher C18 column, 4.6 μm, 150 mm×5 mm) with gradient elution using acetonitrile/ammonium acetate (pH 4.0) as the mobile phase. The formation of rT3 was monitored at λ=275 nm and the amounts of deiodinated products formed in the reactions in the presence or absence of test compounds were calculated by comparing the peak areas.

Inhibition of the DIO3 mimic by TYR-DBRMD (Compound 3)

Compounds 3 and 4 were selected based on their water solubility. The TYR (tyrosine derivative, compound 3) is more soluble in water (due to the presence of —OH and —COOH groups) than PBENZ (benzoic acid derivative, compound 4), but the PBENZ is expected to be more lipophilic. The reactivity of the two compounds toward the DIO3 mimic is was found to be similar, although they may exhibit different binding behavior with the enzyme. However, the affinity data with the mimic may not correlate with that of the enzyme, as there will be additional interactions (hydrogen bonding etc) with the inhibitors at the active site of the enzyme, which are absent with the mimetic molecule.

Figure 5:
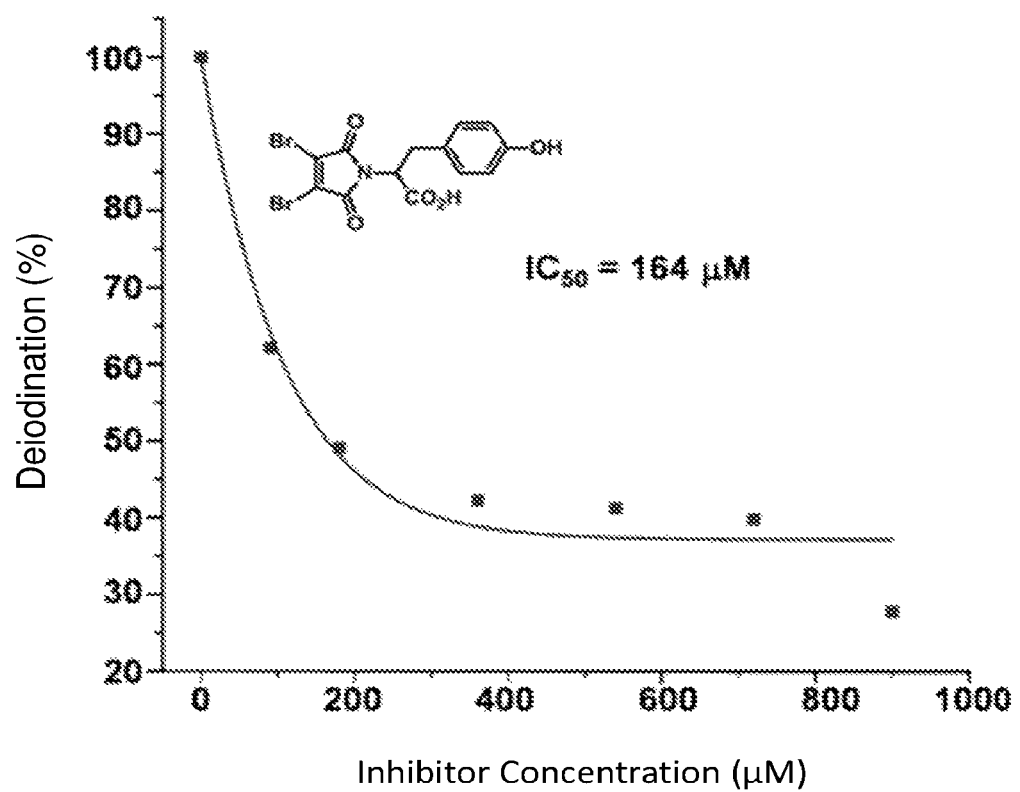
FIG. 5 shows Inhibition of DIO3 mimic by Compound 3 (2,3-dibromo-N-3-(4-hydroxyphenyl)propanoic acid) maleimide; TYR-DBRMD).

The two compounds (3 and 4) react stoichiometrically with the mimic. The IC$_{50}$ values for inhibiting the DIO3 mimic were found to be in the micromolar range (FIG. 5) as the mimics used were in the micromolar concentrations for the deiodination of thyroxine. Assuming that in vivo, the enzymes are present in sub-nanomolar concentrations and the inhibitors are expected to form a covalent bond with the enzyme, it is expected the IC$_{50}$ values will be in the nanomolar concentration range.

Additional inhibitors of DIO3 contemplated by the present invention are compounds 5, 6, 7, 8, 9, 10, 11 and 12 presented below. Those compounds comprise several modifications such as iodine ions (in ITYR-DIBRMD—compound 5, and IOP-DIBRMD—compound 6). These compounds can be stabilized by halogen bonding at the enzyme active sites, caused by the iodine atoms that are attached to maleimide moiety, thus greater deiodinase isoenzyme specificity is supposedly achieved. As DIO3 readily accepts iodinated substrates, the introduction of iodine may help the compounds to bind strongly to the active site. For example, the commercially available iodine-containing compound, Iopanoic acid (IOP) has been shown to be a substrate for DIO3 (Huang MP et al., *Thyroid,* 2011, 21, 1263).

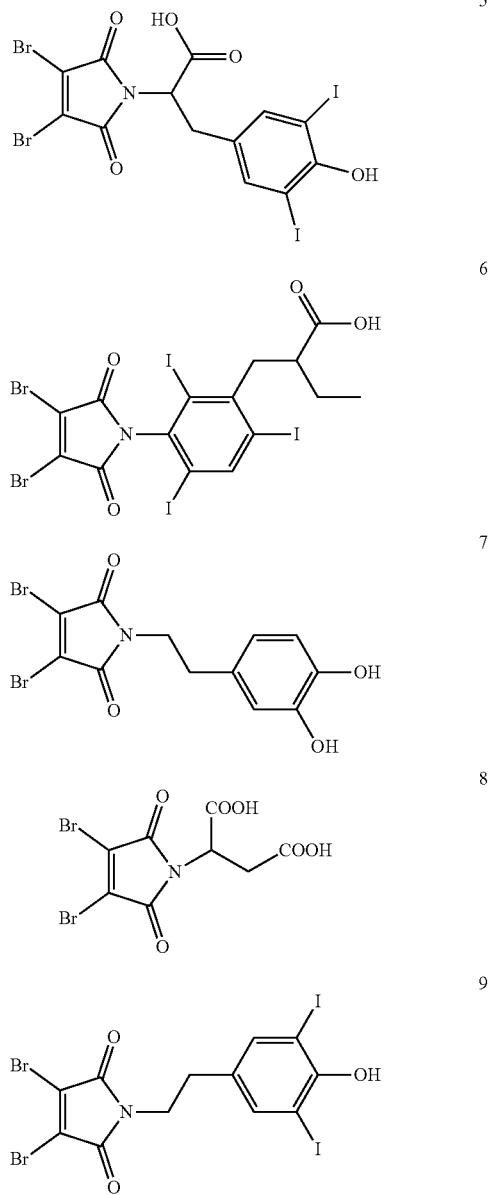

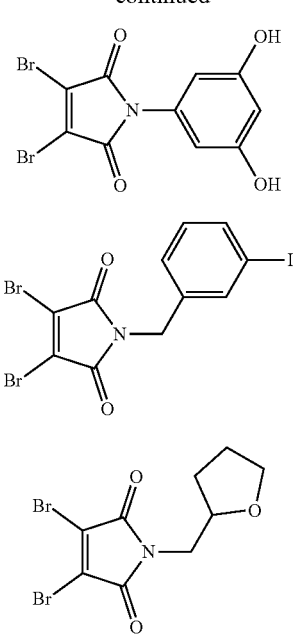

Example 3: High Throughput Assays for Determining Deiodinase 3 Inhibitors Effects on Enzyme Activity Rapid evaluation of the effects of novel putative deiodinase 3 inhibitors on activity levels of DIO3 is established by a high output system employing two main lines of in vitro assays:

1) Mouse brain-derived microsome assay: Mouse brain tissue is homogenized and centrifuged to obtain microsomal fractions. Protein concentration in each fraction pellet is determined by Bradford Assay. Deiodinase 3 activity determination, in the presence of putative deiodinase inhibitors, is carried out by incubation of a given amount of the fraction with the radioligand [3,5-$^{125}$I]T3, each incubation done with blanks (no protein) to correct for non enzymatic degradation of radioligand. Reactions are stopped and radioiodide $^{125}$I emission is measured by precipitation of the [$^{125}$I]iodothyronines and isolation of the emitted (by the inner ring deiodination reaction) $^{125}$I radioiodide on microcolumns. Radioactivity in the eluate is monitored using a scintillation detector.

2) Cell based assay: Astrocytes from neonate mice are harvested and a cell suspension is prepared, plated on Petri dishes and maintained in a cell incubator. After 7 days, cells are disrupted and homogenates are prepared. In the presence of the putative deiodinase 3 inhibitor compound, the homogenates is incubated with [$^{125}$I]T3. Reactions are stopped by the addition of NH$_4$OH containing 10 micro molar T3. The [$^{125}$I]3,3'-T2 produced by deiodinase 3 action is separated from [$^{125}$I]T3 by chromatography. Then the radioactive products of the reaction are counted for determination of D3 activity, expressed as fentomoles of 3,3'-T$_2$ per minute per milligram protein.

Example 4: Effects of Intracerebroventricular (ICV) Administration of ITYR-DIBRMD (ITYR; Compound 5) and IOP-DIBRMD (IOP; Compound 6) on Depression Materials and Methods:
Chronic Intra-cerebroventricular (ICV) administration via osmotic minipumps The intra-cerebroventricular injection was performed via a cannula inserted as follows: first, for the chronic administration of compounds or vehicle, osmotic minipumps (Alzet model 1004 for up to 28 days administration) were employed. Empty minipumps were filled under sterile conditions with 0.1 ml of PBS or with PBS containing either one of the DIO3 inhibitors and then connected to brain infusion kits. The filled minipumps connected to the brain infusion kits were than primed in an incubator at 37° C. before being implanted into the animals. At the surgery itself, each mouse was anaesthetized by intraparenteral (i.p.) injection of anesthesia. The anesthesia solution was prepared as follows: for each 2 ml of solution, 900 µl ketamine plus 100 µl xylazine 2% was supplemented with 1000 µl of 0.9% NaCl saline solution. 70 µl of the anesthesia solution was administered i.p to a 20 gram (about 100 µl for 30 gram) weighing animal. After being anesthetized the animal was hooked to a stereotactic table. A longitudinal cut was made in the head skin, the upper part of the skull was exposed and a hole was produced using 0.5 mm diameter drill and the cannula was inserted. The hole was located at the following coordinates relative to the bregma: Anterior-ventral-dorsal=2.5 mm; Medial-lateral=1.0 mm and anterior-posterior=0.0 mm Thereafter each minipump—was inserted subcutaneously to the interscapular space and the base of the infusion kit cannula was glued, using specialized Loctite adhesive, to the skull base so the cannula shaft itself will protrude through the drilled hole to the lateral ventricle, and through a catheter linked to ALZET brain infusion kits number 3, the compounds or vehicle were intracerebroventricullary through the drilled hole.

The wound formed in the skull was sown with silk sutures, and after it awoke, each animal was transferred to the home cage for recovery, typically for 48 h, after which the experiment may be started.

39 male BALB/c male mice aged 8 weeks were implanted with ALZET model 1004 osmotic minipumps for intracerebroventricular (ICV) administration of compounds in 3 treatment groups (13 mice in each group): (1) the putative DIO3 inhibitor IOP-DIBRMD (IOP, compound 6) dissolved in phosphate buffered solution (PBS) vehicle; (2) the putative DIO3 inhibitor ITYR-DIBRMD (ITYR, compound 5) dissolved in PBS; (3) PBS vehicle. Minipumps contained 0.1 ml of PBS into which the putative DIO3 inhibitors ITYR (5 mg/kg) or IOP (2 mg/kg) were dissolved, or PBS vehicle. 8, 13 and 9 mice survived the experiment in the PBS, ITYR and IOP groups, respectively. Deaths were related to the surgical procedure. After recovery from minipump implantation surgery, animals were returned to their home cages for continuous ICV compound administration for 3 weeks, before behavioral testing commenced.

Assessment of Antidepressant-like Activity and Serum and Brain Thyroid Hormone Levels Novelty Suppressed Feeding Test (NSFT):
After the last treatment administration, all food was removed from the cage for 24 hours (water was available ad libitum). At the end of this period, each animal was introduced into a 50×50×30 (height) cm plastic arena located in a specialized behavioral room in which all behavioral tests were tracked by cameras linked to a computer installed with EthoVision behavioral tracking software of the latest edition (XT 10). A pellet of food was placed on an elevated surface in the center of the arena. Time elapsing from the introduction of the animal into the arena until it commences eating (latency to feed), total distance move, velocity and time spent in the arena periphery (lateral 10 cm on each side) and center were recorded. The animal was then removed from the arena immediately after it begins to eat or after not doing so for 5 min. After the test, the animal was immediately transferred to its home cage and left to consume a previously weighed amount of food for 10 minutes. On completion of this period the food was weighed again to calculate the home cage food consumption. The rating of the animals' behavior was conducted by two experimenters who were blind to the treatment received by each mouse. The mean of the two ratings was calculated and used for the statistical analysis.

Serum and Brain Thyroid Hormone Levels

At the end of the tests, animals were anesthetized with veterinary Pental (13.333 mg/kg) and cardiac blood was drawn for peripheral T3 (triiodothyronine) and T4 (thyroxine) levels. Brains were harvested for evaluating brain T3, T4 levels. Hormone levels in the sera and brains were measured by SunLong Biotech Mouse Ultrasensitivity total and free T3 and T4 ELISA Kits, employing producing a standard curve followed by actual measurement, in which OD levels obtained by spectrophotometer were converted, using the standard curve, to pg/ml values.

Results i) Effect of IOP and ITYR on Brain and Serum Hormone Levels

Figure 10:
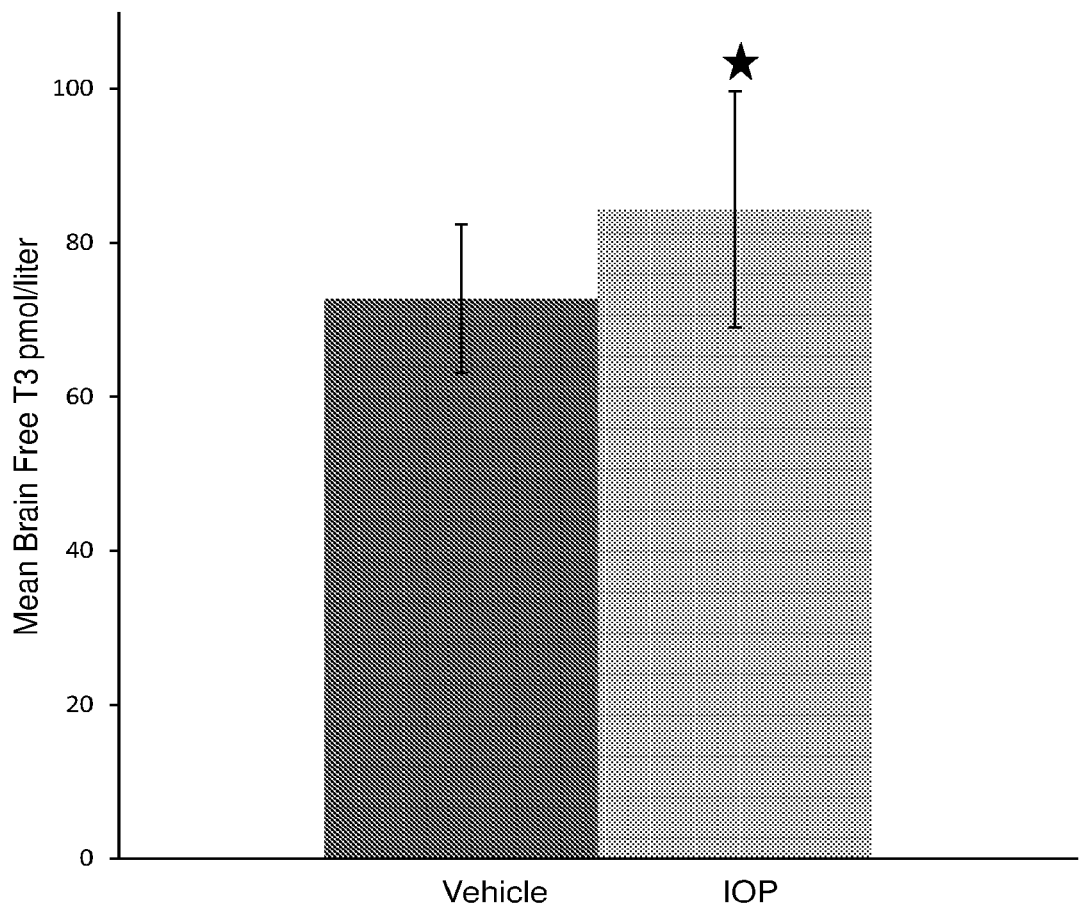
FIG. 10 is a bar graph showing brain T3 levels (pg/ml) following intracerebroventricular (ICV) administration of IOP-DIBRMD (2,3-dibromo-N-2,4,6-triiodobenzyl)butanoic acid)maleimide; IOP, compound 6) by osmotic minipumps for 3 weeks (*Significant; One sided, non-paired t test).

As shown in Table 1 and FIG. 10, IOP treatment for 3 weeks via ICV administration resulted in a significant increase in brain free T3 levels (about 46%). Brain free T3 level was not significantly increased when ITYR was administered. Neither treatment significantly increased brain free T4 levels or the levels of either free hormone in the serum.

TABLE 1

Brain and serum hormone levels after treatment with IOP and ITYR

| | | Free T3 (pg/ml) | | | | | |
|---|---|---|---|---|---|---|---|
| | | Brain | | | Serum | | |
| Treatment | No. of mice | Mean | SD | Signifi-cance* | Mean | SD | Signifi-cance* |
| Vehicle (PBS) | 8 | 72.74 | 9.63 | | 14.45 | 2.83 | |
| IOP | 10 | 84.30 | 15.31 | *0.041 | 12.23 | 1.64 | NS |
| ITYR | 12 | 81.98 | 12.24 | NS | 12.33 | 1.30 | NS |

| | | Free T4 (ng/ml) | | | | | |
|---|---|---|---|---|---|---|---|
| | | Brain | | | Serum | | |
| Treatment | No. of mice | Mean | SD | Signifi-cance* | Mean | SD | Signifi-cance* |
| Vehicle (PBS) | 8 | 250.54 | 53.51 | | 36.05 | 8.53 | |
| IOP | 10 | 244.11 | 44.72 | NS | 35.75 | 9.79 | NS |
| ITYR | 12 | 262.86 | 32.70 | NS | 37.00 | 8.92 | NS |

Figure 11:
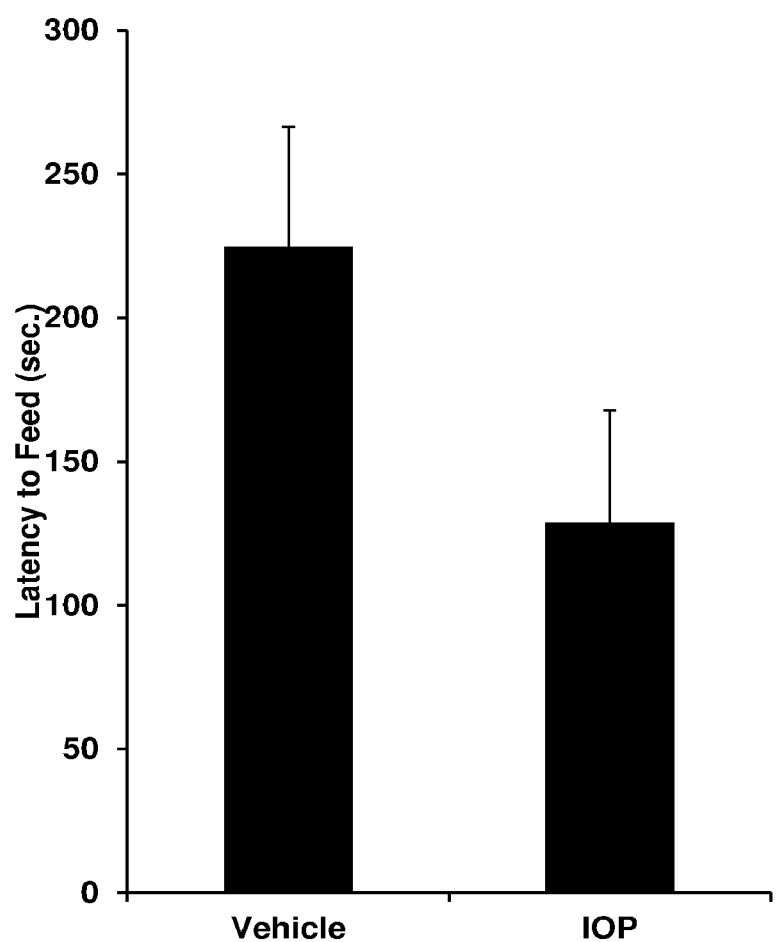
FIG. 11 is a bar graph showing the effect of IOP-DIBRMD (IOP, compound 6) on latency to feed in the novelty suppressed feeding test. Marginal means derived from the ANCOVA are shown. The effect of T3 in the model is significant (F=6.21; p=0.026).
Figure 12:
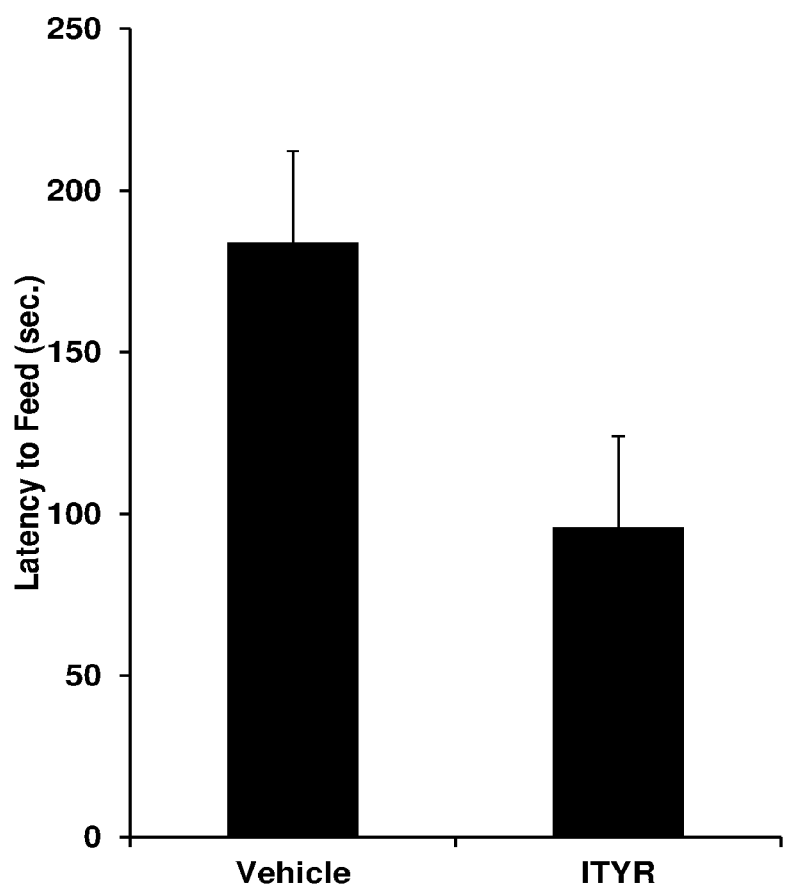
FIG. 12 is a bar graph showing the effect of ITYR-DIBRMD (2,3-dibromo-N-3-(4-hydroxy-3,5-diiodophenyl) propanoic acid) maleimide; ITYR, compound 5) on latency to feed in the novelty suppressed feeding test. Marginal means derived from the ANCOVA are shown. Animals treated with IOP show a reduced latency to feed. Model shows significance (F=7.23; p=0.006). Effect of T3 in the model is significant (F=7.62; p=0.01)

*One sided, non-paired t test; active compound vs. vehicle ii) Effect of IOP and ITYR on Latency to Feed in the Novelty Suppressed Feeding Test The time taken for a rodent to start eating a pellet of food located in the center of an open field arena (latency to feed) is a reflection of anxiety level and is also seen as reflecting level of anhedonic behavior. In the current experiment, treatment with both IOP and ITYR resulted in a reduced latency to feed compared to mice treated with vehicle (FIGS. 11 and 12, respectively). Data were analyzed by analysis of covariance with brain T3 level entered as the covariate. The effect of T3 in mice treated with both IOP and ITYR was found to be significant.

Example 5: Effect of DIO3 Inhibitors on Ovarian Cancer Cells

Cell lines: Human ovarian adenocarcinoma cells employed in the study were OVCAR-3 (ATCC HTB-161), A2780 (Sigma Aldrich) and SKOV-3 (ATCC HTB-77). Human normal embryonic kidney cells, HEK 293 (ATCC CRL1573) were used. All cells were cultured in RPMI1640 supplemented with 10% heat-inactivated FBS and antibiotics. Before conducting an experiment, cells were cultured for 24 h in RPMI1640 supplemented with 1.5% heat-inactivated charcoal stripped FBS and antibiotics.

Flow cytometry (MACSQuant, Miltenyi): The cells were treated with 70% ethanol at −20° C. for 1 hour, stained with rabbit anti Human DIO3 monoclonal antibody (Alexa Fluor (R) 647) from Novus Biologicals and analyzed for endogenous DIO3 level by FACS.

Viability: WST-1 (Roche; 10% final concentration) was incubated with cells at 37° C. for 2 h and read with a MicroELISA reader at 440 nm.

Microscopy: The cells were visualized using a microscope equipped with a camera (model IX71; Olympus) with a 20_/0.50 objective lens and Cell^A (version 3.1) Olympus software imaging.

Compounds

The following DIO3 inhibitory compounds were examined: PBENZ (compound 4); TYR (compound 3); IOP (compound 6); ITYR (Compound 5): DOP (compound 7) and ASP (compound 8).

The anti cancerous (anti-proliferative) effect of the DIO3 inhibitors described above was examined using the above-described human ovarian cancer cells (OVCAR3, SKOV3 and A2780). The cells were cultured in RPMI 1640/10% FBS/antibiotics.

Figure 13A:
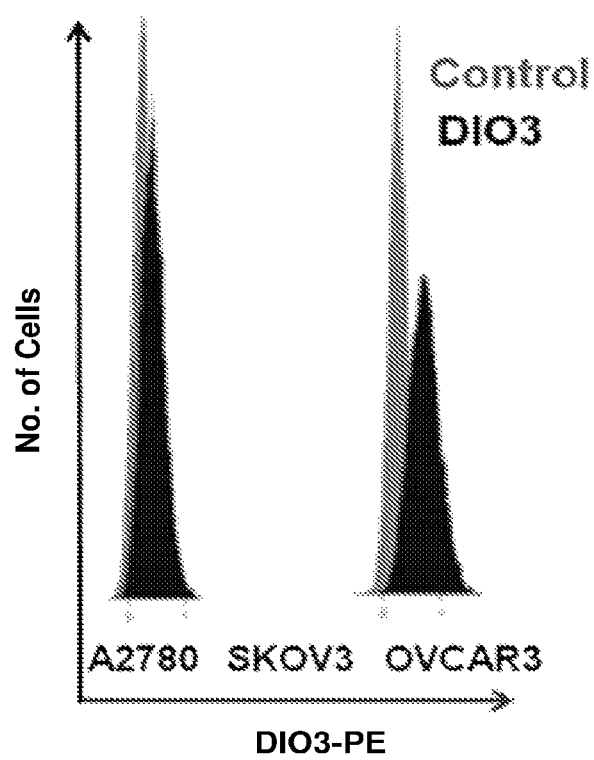
FIG. 13A shows DIO3 expression in ovarian cancer cells (A2780, SKOV3 and OVCAR3 cell lines) as measured by FACS analysis.

T3 influences cellular growth, differentiation and apoptosis, and thus its level within cells is strictly regulated. Elevated DIO3 levels and thus reduced T3 levels are favorable to the neoplastic process. Therefore, cancer cells that show elevated DIO3 are a good model for testing the potential anti-neoplastic efficacy of DIO3 inhibitors. Accordingly, the level of endogenous DIO3 protein in the different cancer cells was assessed by FACS analysis using monoclonal antibody against the human DIO3. Results indicate that OVCAR3 cells exhibited the highest DIO3 protein level (FIG. 13A) and this cell type was used as the experimental model.

Figure 13B:
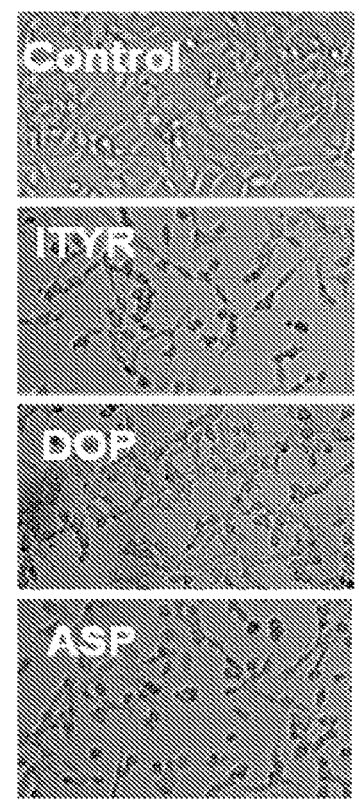
FIG. 13B demonstrated the effect of compounds C1-C6 on the density of the ovarian cancer cell line OVCAR3. Cells were treated with 0.5 µM DIO3 inhibitors for 48 h and imaged by light microscopy.
Figure 13C:
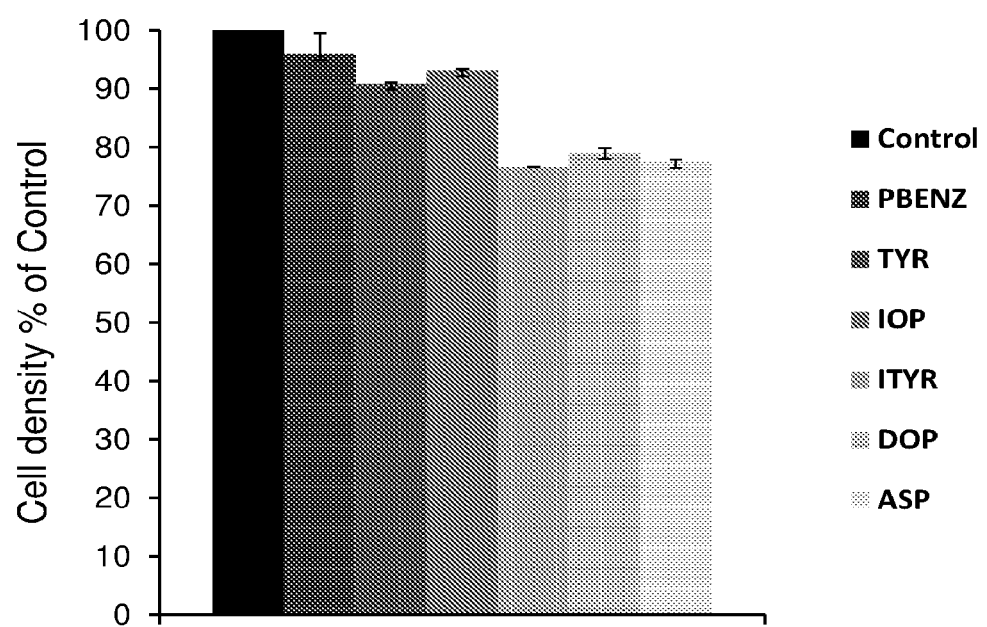
FIG. 13C demonstrated the effect of compounds C1-C6 on the viability of the ovarian cancer cell line OVCAR3. Cells were treated with 0.5 µM DIO3 inhibitors for 48 h and analyzed by WST-1 viability assay.

OVCAR3 cells were collected and seeded in 96 well plates (10,000/well). The six compounds were then dissolved in DMSO and added to a final 0.5 μM concentration for 48 h of incubation. After incubation the cells were imaged by light microscopy (FIG. 13B). A marked reduction in cell density and deformed cell morphology was observed with three agents, ITYR, DOP and ASP. These cells were then examined for cell viability by WST-1 assay (FIG. 13C). No effect was evident using PBENZ, a low reduction in viability was observed using TYR and IOP and a significant reduction in cell viability by the same 3 agents described above, ITYR, DOP and ASP was shown.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating ovarian cancer, comprising the step of administering to a subject in need thereof a therapeutically effective amount of at least one compound selected from the group consisting of:

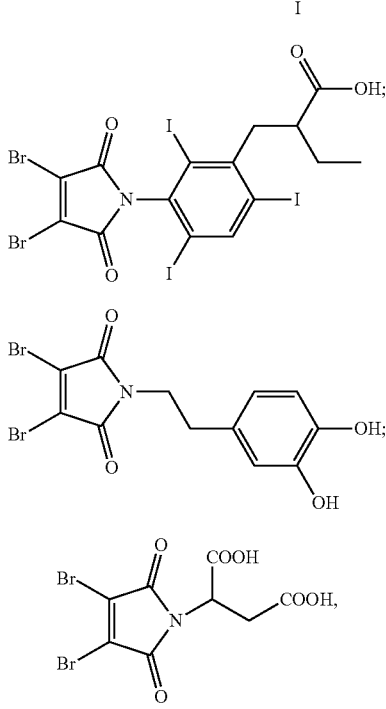

and salts thereof, or a pharmaceutical composition comprising said compound and a pharmaceutically acceptable carrier or excipient.

2. The method according to claim 1, wherein the compound is represented by the structure of formula 4:

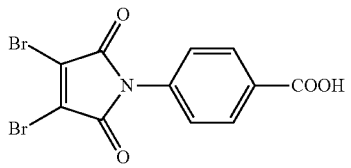

4 or a salt thereof.

3. The method according to claim 1, wherein the compound is represented by the structure of formula 5:

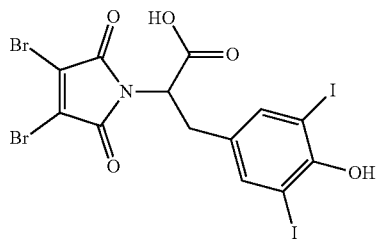

5 or a salt thereof.

4. The method according to claim 1, wherein the compound is represented by the structure of formula 6:

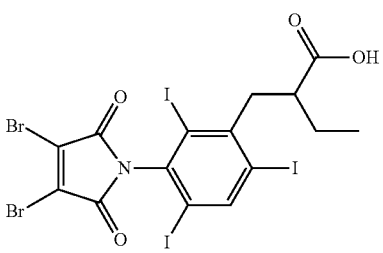

6 or a salt thereof.

5. The method according to claim 1, wherein the compound is represented by the structure of formula 7:

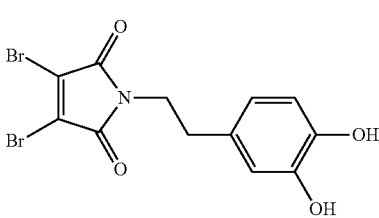

7 or a salt thereof.

6. The method according to claim 1, wherein the compound is represented by the structure of formula 8:

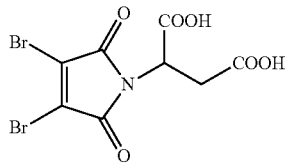

8 or a salt thereof.

7. The method according to claim 1, wherein the ovarian cancer is associated with aberrant Type III deiodinase (DIO3) expression or activity.

8. The method according to claim 7, wherein the compound inhibits the activity of Type III deiodinase (DIO3).

9. The method according to claim 8, wherein inhibition of the DIO3 activity results in increased amount of T3 in the subject.

10. The method according to claim 1, wherein the ovarian cancer is a high grade ovarian cancer.

11. A method of attenuating Type III deiodinase (DIO3) expression and/or activity, comprising the step of contacting the enzyme with an effective amount of at least one compound selected from the group consisting of:

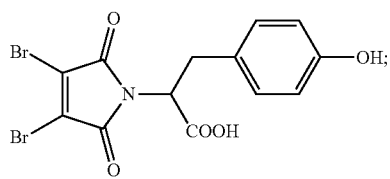

3

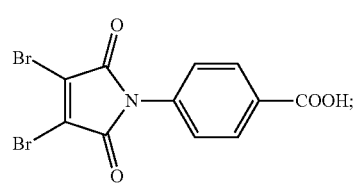

4

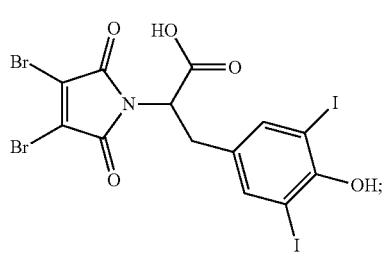

5

-continued

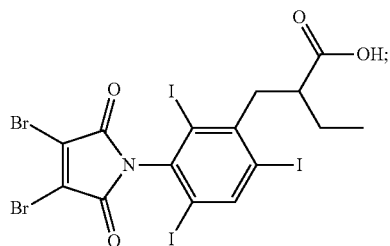

6

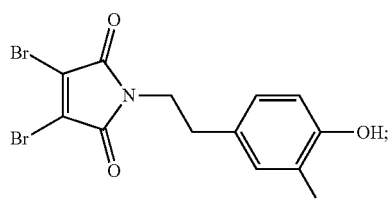

7

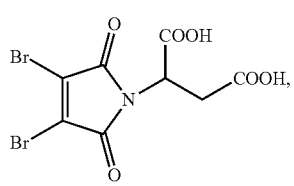

8 and salts thereof, or a pharmaceutical composition comprising said compound and a pharmaceutically acceptable carrier or excipient.

12. The method according to claim 11, wherein attenuating DIO3 expression and/or activity results in treatment of ovarian cancer in a subject.

13. The method according to claim 11, wherein the compound is represented by the structure of formula 4:

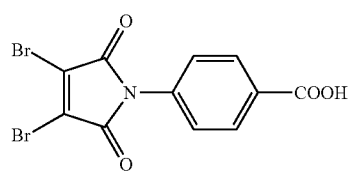

4 or a salt thereof.

14. The method according to claim 11, wherein the compound is represented by the structure of formula 5:

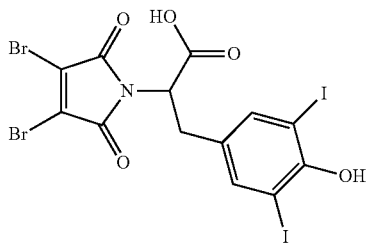

5 or a salt thereof.

15. The method according to claim 11, wherein the compound is represented by the structure of formula 6:
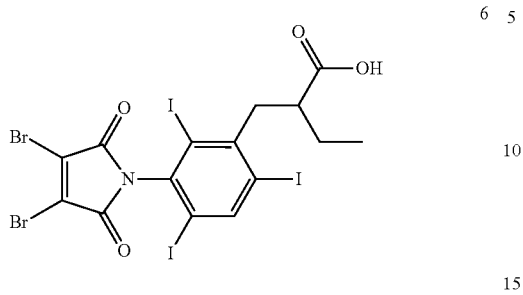
or a salt thereof.
16. The method according to claim 11, wherein the compound is represented by the structure of formula 7:
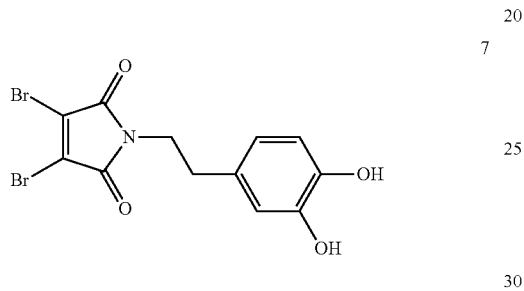
or a salt thereof.
* * * * *

UNITED STATES PATENT AND TRADEMARK OFFICE
CERTIFICATE OF CORRECTION

PATENT NO. : 11,091,434 B2
APPLICATION NO. : 16/553647
DATED : August 17, 2021
INVENTOR(S) : Bernard Lerer et al.

Page 1 of 1

It is certified that error appears in the above-identified patent and that said Letters Patent is hereby corrected as shown below:

On the Title Page

Item (72) should be corrected to read:
Inventors: Bernard Lerer, Alon Shvut (IL);
        Mugesh Govindasamy, Bangalore (IN);
        Tzuri Lifschytz, Jerusalem (IL);
        Osnat Ashur-Fabian, Zur-Moshe (IL)

Signed and Sealed this
Eleventh Day of March, 2025

Coke Morgan Stewart
*Acting Director of the United States Patent and Trademark Office*